(12) United States Patent
Luo et al.

(10) Patent No.: US 9,770,486 B2
(45) Date of Patent: *Sep. 26, 2017

(54) METHODS OF NEUROPROTECTION INVOLVING MACROPHAGE COLONY STIMULATING FACTOR RECEPTOR AGONISTS

(71) Applicants: The Board of Trustees of the Leland Stanford Junior University, Stanford, CA (US); The United States of America represented by the Department of Veterans Affairs, Washington, DC (US)

(72) Inventors: Jian Luo, Palo Alto, CA (US); Anton Wyss-Coray, Palo Alto, CA (US)

(73) Assignees: The Board of Trustees of the Leland Stanford Junior University, Stanford, CA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/849,176

(22) Filed: Sep. 9, 2015

(65) Prior Publication Data
US 2016/0143996 A1 May 26, 2016

Related U.S. Application Data

(63) Continuation of application No. 13/441,879, filed on Apr. 7, 2012, now Pat. No. 9,161,968.

(60) Provisional application No. 61/473,328, filed on Apr. 8, 2011.

(51) Int. Cl.
*A61K 38/20* (2006.01)
*A61K 38/00* (2006.01)
*A61K 38/19* (2006.01)

(52) U.S. Cl.
CPC .......... *A61K 38/20* (2013.01); *A61K 38/193* (2013.01)

(58) Field of Classification Search
None
See application file for complete search history.

(56) References Cited

U.S. PATENT DOCUMENTS

| | | | |
|---|---|---|---|
| 7,785,601 B2 | 8/2010 | Schaebitz et al. | |
| 2004/0141946 A1 | 7/2004 | Schaebitz et al. | |
| 2011/0243947 A1* | 10/2011 | Doody | A61K 39/39541 424/139.1 |
| 2013/0302322 A1* | 11/2013 | Wong | C07K 16/2869 424/133.1 |
| 2017/0081415 A1* | 3/2017 | Wong | C07K 16/2866 |

OTHER PUBLICATIONS

Lin 2008 "discovery of a cytokine and its receptor by functional screening of the extracellular proteome" science 320:807-811.*
Yamane 2014 "csf-1 receptor-mediated differenetiation of a new type of monocytic cell with b cell-stimulating activity: its selective dependence on il-34" J leukoc biol 95(1):19-31.*
McLaurin, JoAnne, Richard Ransohoff and Marco Prinz. "Microglial pilgrimage to the brain", Nature Medicine, vol. 16, No. 12, Dec. 2010, pp. 1380-1381.
Boissonneault et al., Powerful beneficial effects of macrophage colony-stimulating factor on beta-amyloid deposition and cognitive impairment in Alzheimer's disease, Brain 2009:132, pp. 1078-1092.
Fedoroff et al., Role of Colony Stimulating Factor-1 in Brain Damage Caused by Ischemia, Neuroscience & Biobehavioral Reviews 1997:21, pp. 187-191.
Vincent et al., Macrophage colony stimulating factor prevents NMDA-induced neuronal death in hippocampal organotypic cultures, Journal of Neurochemistry 2002:82, pp. 1388-1397.
Mitrasinovic et al., Microglia Overexpressing the Macrophage Colony-Stimulating Factor Receptor Are Neuroprotective in a Microglia-Hippocampal Organotypic Coculture System, The Journal of Neuroscience 2005:25, pp. 4442-4451.
Berezovskaya et al., Colony stimulating factor-1 potentiates neuronal survival in cerebral cortex ischemic lesion, Acta Neuropathol 1996:92(5), pp. 479-486.
Wang et al., Expression of colony stimulating factor-1 receptor (CSF-1R) by CNS neurons in mice, J Neurosci Res 1999:57(5), pp. 616-632.
Yagihashi et al., Macrophage colony stimulating factor (M-CSF) protects spiral ganglion neurons following auditory nerve injury: morphological and functional evidence, Exp Neural 2005:192(1), pp. 167-177.
Gowing et al., Macrophage colony stimulating factor (M-CSF) exacerbates ALS disease in a mouse model through altered responses of microglia expressing mutant superoxide dismutase, Exp Neural 2009:220(2), pp. 267-275.
Mizuno et al., Interleukin-34 selectively enhances the neuroprotective effects of microglia to attenuate oligomeric amyloid-beta neurotoxicity, Am J Pathol 2011:179(4), pp. 2016-2027.

* cited by examiner

*Primary Examiner* — Adam M Weidner
(74) *Attorney, Agent, or Firm* — Casimir Jones, S.C.

(57) ABSTRACT

Disclosed are novel methods for preventing or attenuating neuronal damage or stimulating neuronal repair, prior to or following central nervous system injury associated with acute or chronic nervous system injury. Macrophage colony stimulating factor receptor agonists including macrophage colony stimulating factor (M-CSF or CSF-1), interleukin-34 (IL-34), proteins or biologically active fragments thereof, peptides or biologically active fragments thereof, peptidomimetics, or small molecules, and the like are effective for prevention or treatment of acute nervous system injury or chronic nervous system injury involving Alzheimer's disease, Parkinson's disease, amyotrophic lateral sclerosis, Huntington's disease, and the like.

15 Claims, 19 Drawing Sheets

Culture media     NMDA (100uM)     NMDA + MCSF     NMDA + IL34

SEQUENCE LISTING

<160> NUMBER OF SEQ ID NOS: 1

<210> SEQ ID NO 1
<211> LENGTH: 48
<212> TYPE: DNA
<213> ORGANISM: Artificial Sequence
<220> FEATURE:
<223> OTHER INFORMATION: Primer

<400> SEQUENCE: 1
gttcatggtg gccgtgcgtg tgccaacatc attgctggcc acacaaga        48

METHODS OF NEUROPROTECTION INVOLVING MACROPHAGE COLONY STIMULATING FACTOR RECEPTOR AGONISTS

CROSS-REFERENCE TO RELATED APPLICATION

This application is a continuation application of U.S. patent application Ser. No. 13/441,879, filed Apr. 7, 2012, now U.S. Pat. No. 9,161,968, which application claims priority to U.S. Provisional Patent Application Ser. No. 61/473,328, filed Apr. 8, 2011, the disclosures of which applications are herein incorporated by reference.

STATEMENT OF GOVERNMENT SUPPORT

This invention was made with government support under AG23708 awarded by the National Institutes of Health. The government has certain rights in the invention.

INCORPORATION OF SEQUENCE LISTING

A computer readable form of the sequence listing, "ASB036UTL_ST25.txt", submitted via EFS-WEB, is herein incorporated by reference.

TECHNICAL FIELD OF THE INVENTION

The present invention relates to methods of attenuating neuronal damage and stimulating neuronal repair involving the administration of agents that activate the macrophage colony stimulating factor receptor.

BACKGROUND

Traumatic brain injury, cerebral ischemia, metabolic insults such as glucose deprivation and oxidative stress as well as neurodegenerative disorders can cause permanent neurological damage and are a major cause of mortality and morbidity. Neuronal damage, leading to acutely injured or degenerating neurons, can also result from aberrant, excessive stimulation of neurons through excitatory neurotransmitters (excitotoxicity), in particular by the excitatory neurotransmitter glutamate.

Neuroprotective factors such as the nerve growth factor, brain-derived neurotrophic factor, neurotrophin-3, neurotrophin-4, novel neurotrophin-1 or insulin-like growth factor 1 (IGF-1) play an important role in the maturation, function, repair and survival of neurons (Sofroniew et al., 2001). Neuronal expression of neuroprotective factors has been found to be markedly upregulated following seizures, cerebral ischemia and other brain injuries, initiating a cascade of events in neurons and surrounding glia cells to prevent further brain damage.

The knowledge about neuroprotective factors has to date not translated into effective treatments following neuronal insults and, as a result, current therapies for traumatic brain injury, ischemic stroke and neurodegenerative disorders are inadequate and not sufficient to stop neuronal cell loss and death. It would, therefore, be highly desirable to have therapeutic agents available for immediate treatment following brain injuries or even prior to brain injuries to mitigate or to prevent neuronal cell death.

SUMMARY OF THE INVENTION

The present invention provides methods for reducing neuronal damage and stimulating neuronal repair following acute or chronic injury of nerve cells of the central nervous system. The methods for attenuating neuronal damage and stimulating neuronal repair following acute or chronic injury of nerve cells of the central nervous system comprise the administration of macrophage colony stimulating factor receptor agonists locally at or near a site of injury or systemically in a therapeutically effective amount and within a time period following acute or chronic injury that is sufficient to provide a therapeutic effect.

Furthermore, the present invention provides methods for preventing or attenuating neuronal damage prior to acute or chronic injury of nerve cells of the central nervous system. The methods for preventing or attenuating neuronal damage prior to acute or chronic injury of nerve cells of the central nervous system comprise the administration of macrophage colony stimulating factor receptor agonists locally or systemically in a therapeutically effective amount and within a time period prior to acute or chronic injury that is sufficient to provide a therapeutic effect.

In one aspect of the present invention, the macrophage colony stimulating factor receptor agonist is a protein or a biologically active fragment thereof; a peptide or a biologically active fragment thereof, a peptidomimetic, or a small molecule. In one embodiment of the present invention, the macrophage colony stimulating factor receptor agonist is the macrophage colony stimulating factor, M-CSF or CSF-1. In another embodiment of the present invention, the macrophage colony stimulating factor receptor agonist is Interleukin-34, IL-34.

The above summary is not intended to include all features and aspects of the present invention nor does it imply that the invention must include all features and aspects discussed in this summary.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

The target quadrant was quadrant 1 in panel D and panel F. Bars are mean±SEM. **, P<0.01; *, P<0.05 compared by ANOVA and Bonferroni post-hoc test.

Figure 2:
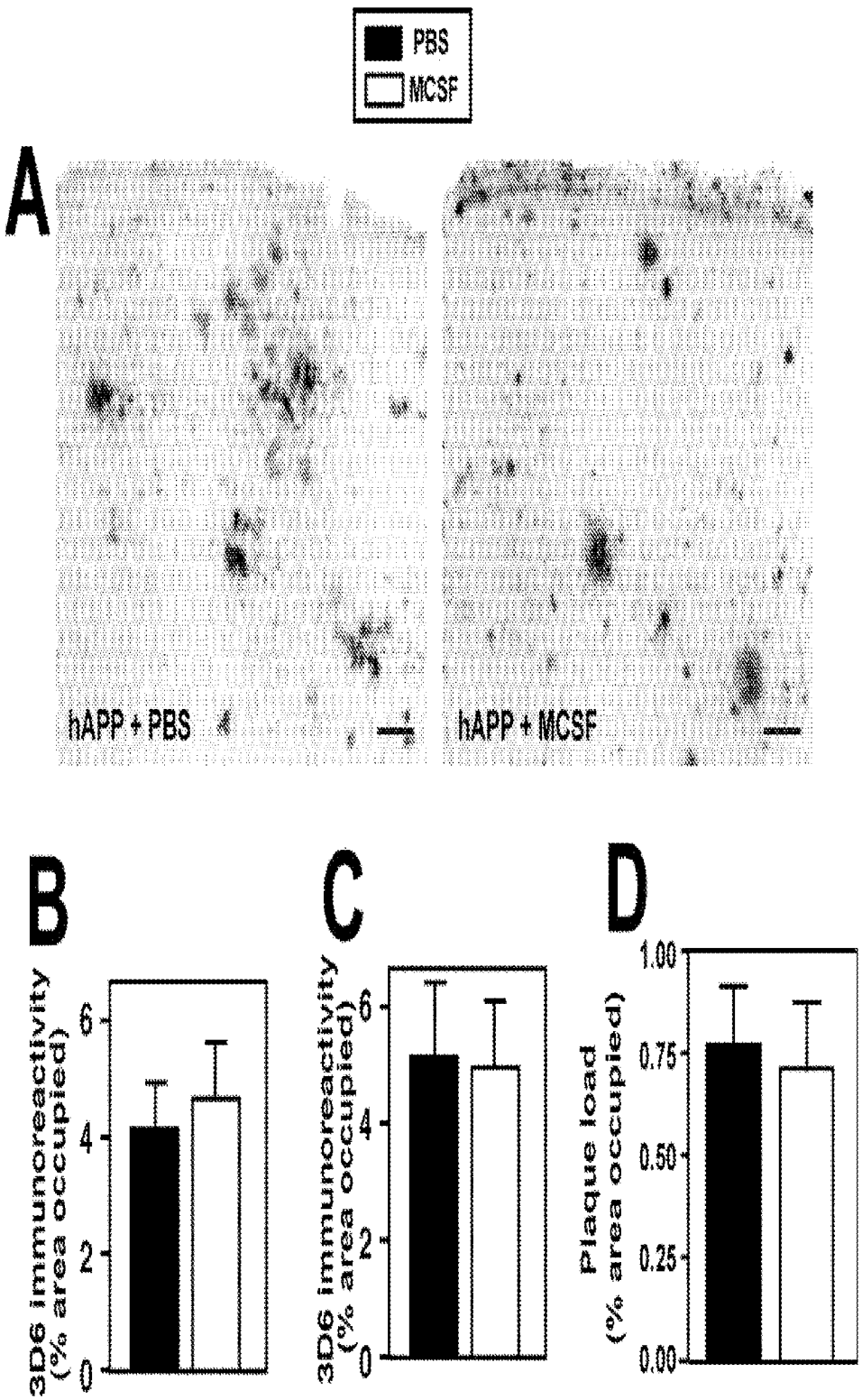

FIG. 2 illustrates that M-CSF treatment does not affect cerebral Aβ deposition in hAPP-transgenic mice, as further described in Example 1. HAPP mice and their wildtype (WT) littermates (n=9-10 mice per genotype, 5.5-6.5 months of age) were injected M-CSF or PBS (i.p., 800 μg/kg) three times a week for 10 weeks. Mice were sacrificed and one hemibrain was fixed for immunohistochemistry. Aβ deposition in brain sections was assessed with antibody 3D6 ($Aβ_{1-5}$) in hAPP mice. In panel A, representative images from mice treated with M-CSF or PBS as control are shown. Scale bar is 40 μm. Quantification of Aβ deposits, expressed as 3D6 immunoreactivity in the cortex (panel B) and the hippocampus (panel C). In panel D, quantification of thioflavin-S staining of hippocampal amyloid plaques is shown, expressed as percentage of hippocampal area covered by plaques. No significant differences were found between M-CSF or PBS treated groups.

Figure 3:
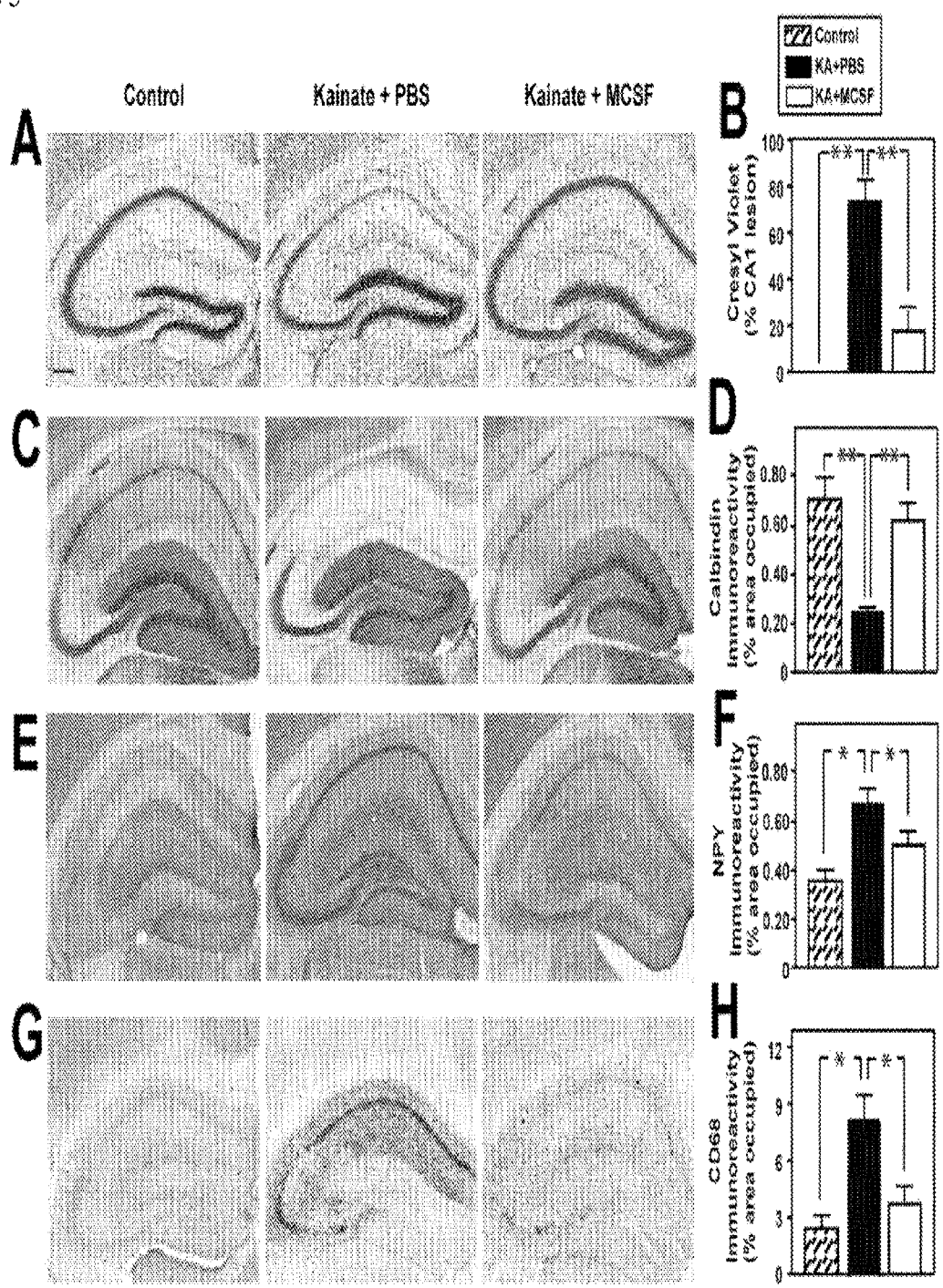

FIG. 3 illustrates that systemic M-CSF attenuates kainic acid-induced neurodegeneration, as further described in Example 2. Two-month-old FVB/N mice were lesioned with kainic acid (20 mg/kg, subcutaneous injection) and sacrificed 5 days later. Recombinant M-CSF (800 μg/kg) was injected intraperitoneally once 24 h before kainic acid. Kainic acid-induced neuronal injury was assessed by cresyl violet staining (A, B), calbindin immunostaining (C, D) and Neuropeptide Y (NPY) immunostaining (E, F), and microglial activation was assessed by CD68 immunostaining (G, H). Representative images are shown from hippocampi of mice left untreated (control, left), kainic acid lesioned and treated with PBS (middle) or M-CSF (right). Scale bar=200 μm. Bars in (B, D, F, and H) are mean±SEM (n=4-7 mice/group). **, P<0.01; *, P<0.05 compared by ANOVA and Bonferroni post-hoc test. Similar results were obtained from three independent experiments.

Figure 4:
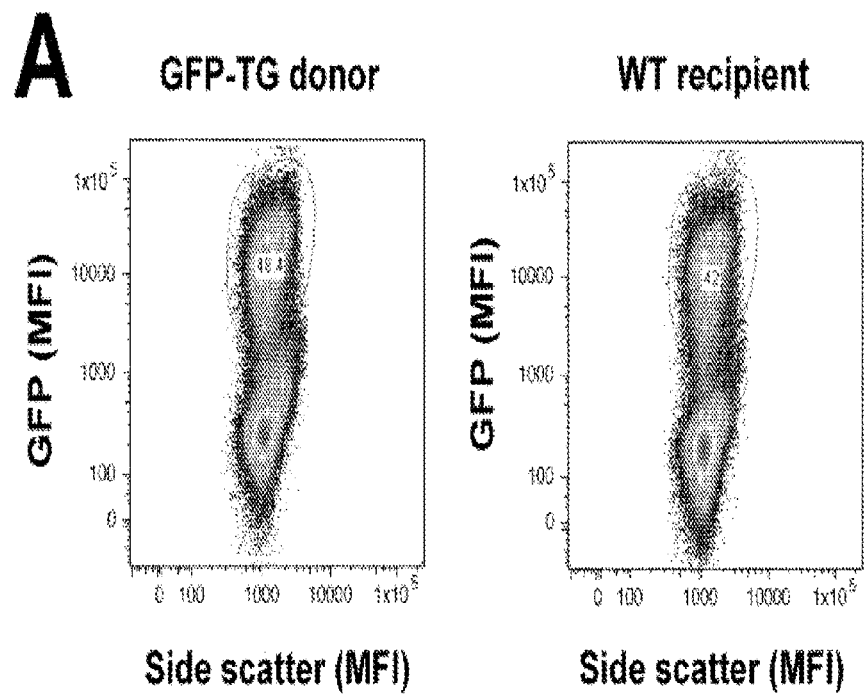
Figure 4:
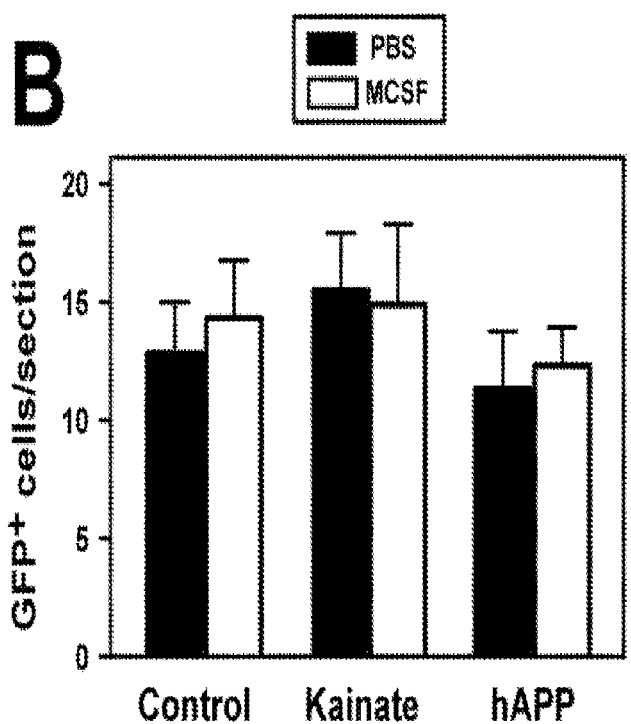

FIG. 4 illustrates that M-CSF does not enhance peripheral cell infiltration, as further described in Example 3. Actin-GFP mice (donor) were paired with wildtype littermates or hAPP mice (recipient) by parabiosis. In panel A, blood was collected 2 weeks after surgery and cells were analyzed by flow cytometry for GFP expression. Representative plots showing similar frequencies of GFP+ cells in the transgenic donor and wildtype recipient at the time of blood collection. MFI, mean fluorescence intensity. Panel B shows the number of GFP+ cells in the brains of recipient parabionts 6 weeks after surgery. In the control and hAPP groups, both parabionts received M-CSF or PBS for 4 weeks. In the kainic acid group, parabionts received one dose of M-CSF or PBS 24 h before KA injection and were sacrificed at day 5 after KA administration. n=3-5 mice per group, 3 sections per mouse.

Figure 5:
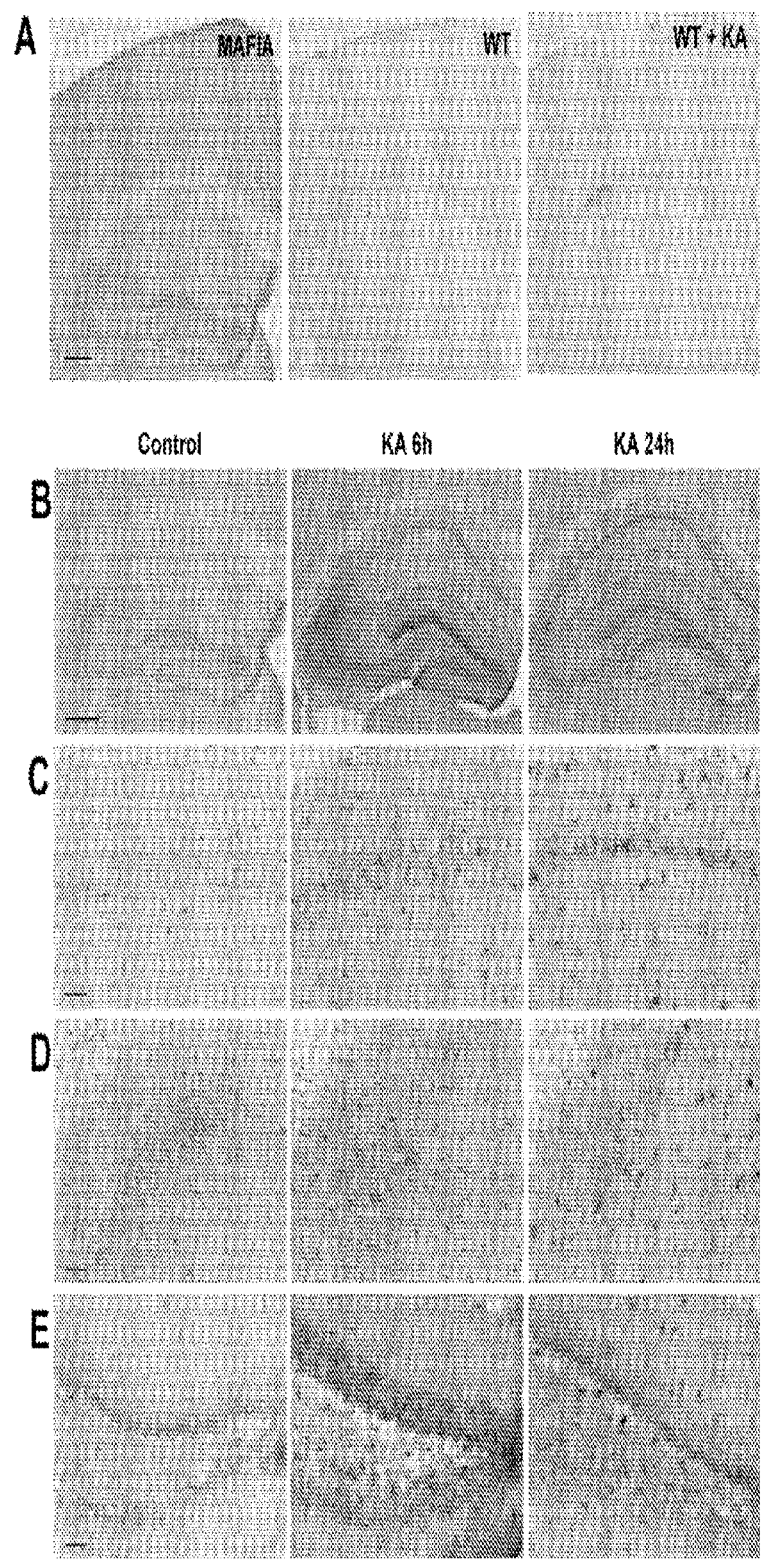

FIG. 5 illustrates that c-Fms reporter gene is upregulated after systemic kainate injury, as further detailed in Example 4. c-Fms reporter mice (MAFIA mice, 2 month of age) were lesioned with kainic acid (20 mg/kg, subcutaneous injection) and sacrificed 6 and 24 h later. These mice express an EGFP tag under the control of the c-fms promoter so that the expression of c-Fms can be detected by EGFP immunostaining. (A) To test the specificity of the antibody against EGFP, brain sections from MAFIA mice (left panel), wildtype mice (middle panel) and wildtype mice with kainate injury (right panel) were immunostained. Note EGFP immunoreactivity is observed only in the EGFP-expressing MAFIA mice, but not in the wildtypes. (B-E) Representative brain images shown from left to right were from controls (no injury), kainic acid lesioned and sacrificed at 6 h, and kainic acid lesioned and sacrificed at 24 h. Areas representing the CA1 (C), CA3 (D) and dentate gyrus (E) are shown at higher magnification. Scale bars=200 μm in (A-B), =50 μm in (C-E).

Figure 6:
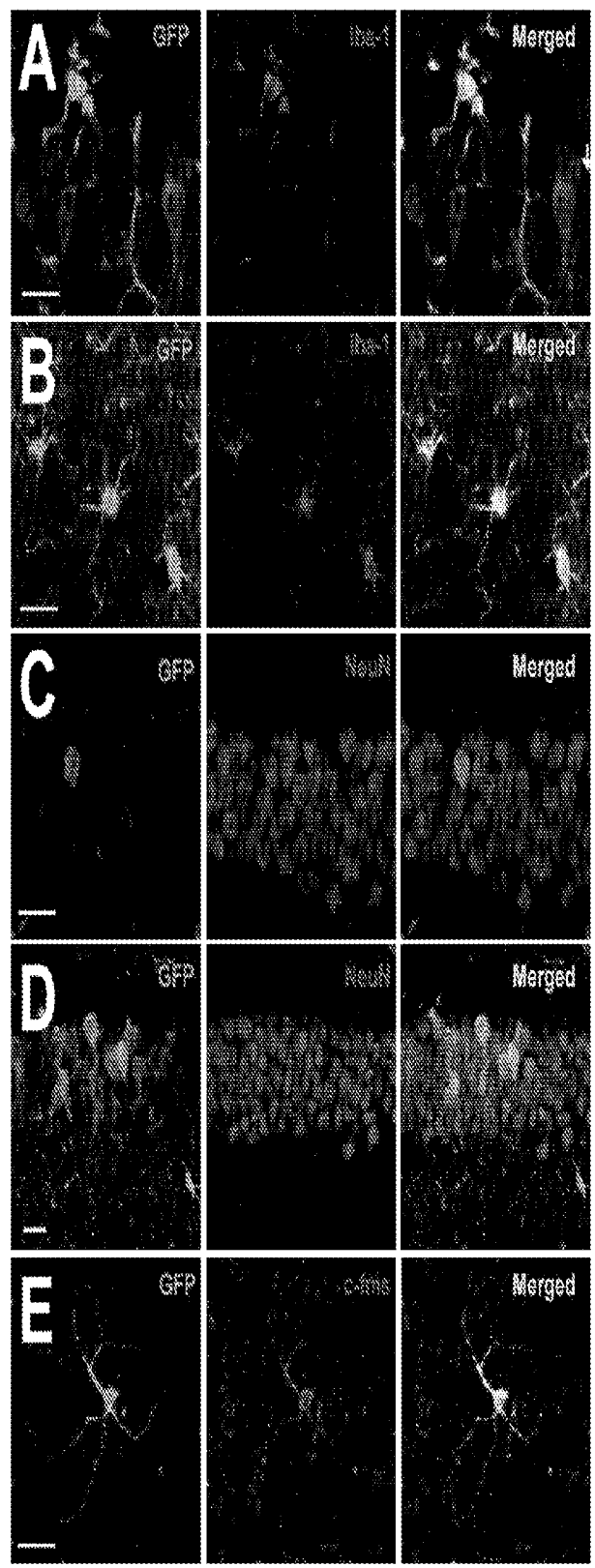

FIG. 6 illustrates that a c-Fms reporter gene is expressed in neurons and upregulated after excitotoxic brain injury, as further detailed in Example 4. c-Fms reporter mice (MAFIA mice, 2 month of age) were lesioned with kainic acid (20 mg/kg, subcutaneous injection) and sacrificed 6 h later. Brain sections from control (A, C) and kainate-lesioned (B, D) were double immunolabeled with antibodies against EGFP (green) and cell type-specific markers Iba-1 (microglia, A, B) and NeuN (neurons, C, D) (red) and images were taken by a confocal microscope. The reporter gene expressing cells appear yellow after superimposition. Note an Iba-1 immuno-negative cell expresses the reporter gene (arrow) in (A). The upregulation of reporter gene in neurons is shown after kainate lesion (D) compared with control (C). Scale bar=20 μm. (E) In situ hybridization with digoxigenin (DIG)-labeled probe for cfms in cultured primary neurons. The hybridization signal (red) was detected by HNPP Fluorescent Detection Set.

Figure 7:
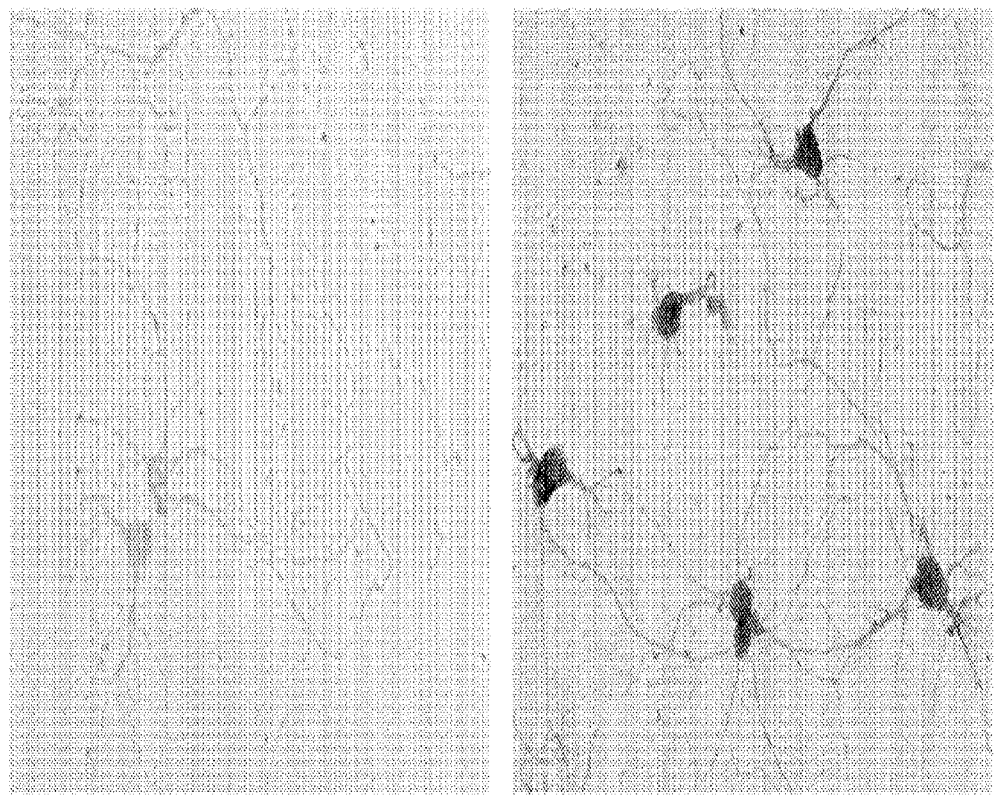

FIG. 7 illustrates in situ hybridization with digoxigenin (DIG)-labeled probe for c-fms in cultured primary neurons, as further detailed in Example 4. Primary hippocampal neurons were isolated from 16 days old CF1 mouse embryos, aged for 6-7 days and hybridized with c-fms probe. Strong hybridization signal was observed in neurons with the anti-sense probe (right panel), but not the sense probe (left panel).

Figure 8:
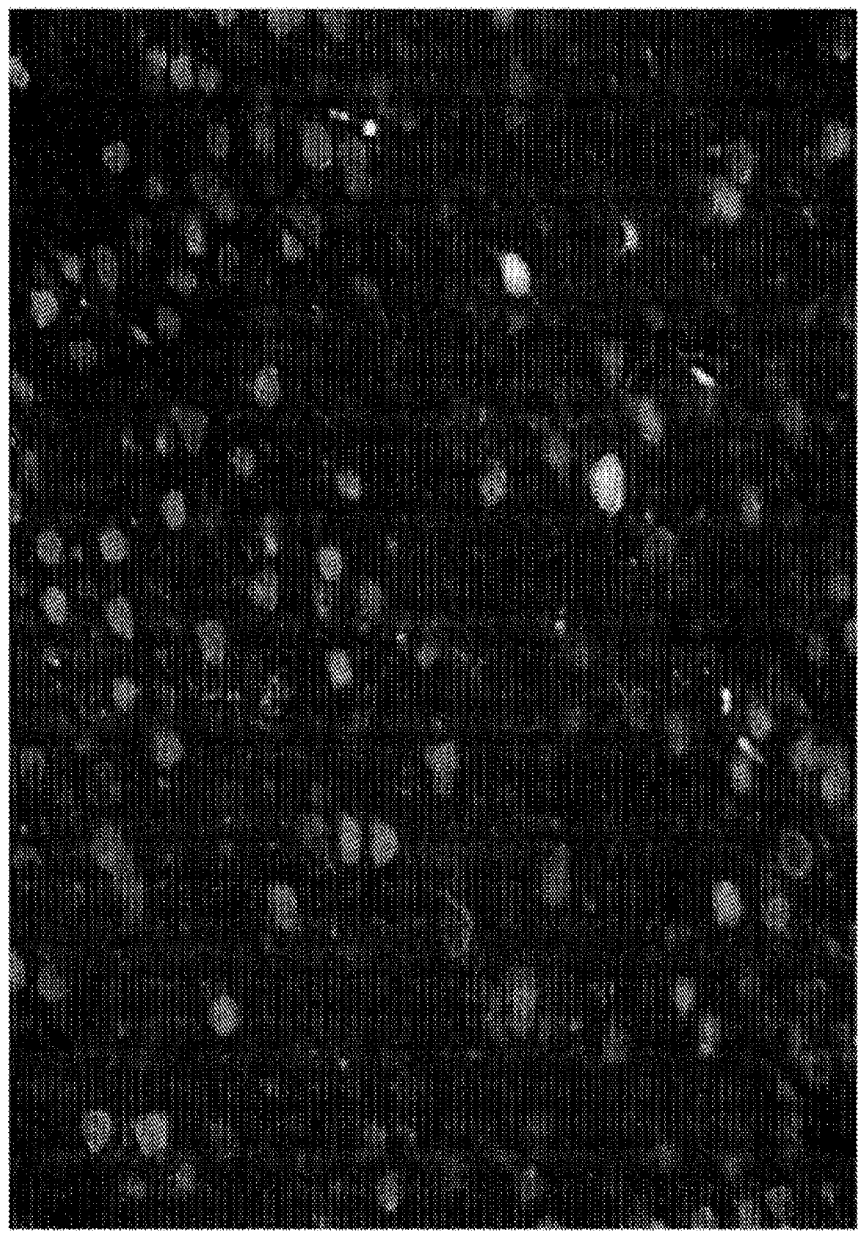

FIG. 8 illustrates that mature neurons express c-fms-driven reporter gene, as further detailed in Example 4. Confocal microscope image showing frontal cortex from a c-fms-iCre×ROSA-stop$^{flox}$-CFP mouse immunolabeled with an antibody against NeuN (red) and stained with DAPI (blue). Cre recombinase expression driven by the endogenous c-fms promoter leads to recombination and deletion of the stop codon in front of Cyan fluorescent protein (CFP). Two bright yellow cells in the image show CFP colocalization with NeuN in mature neurons.

Figure 9:
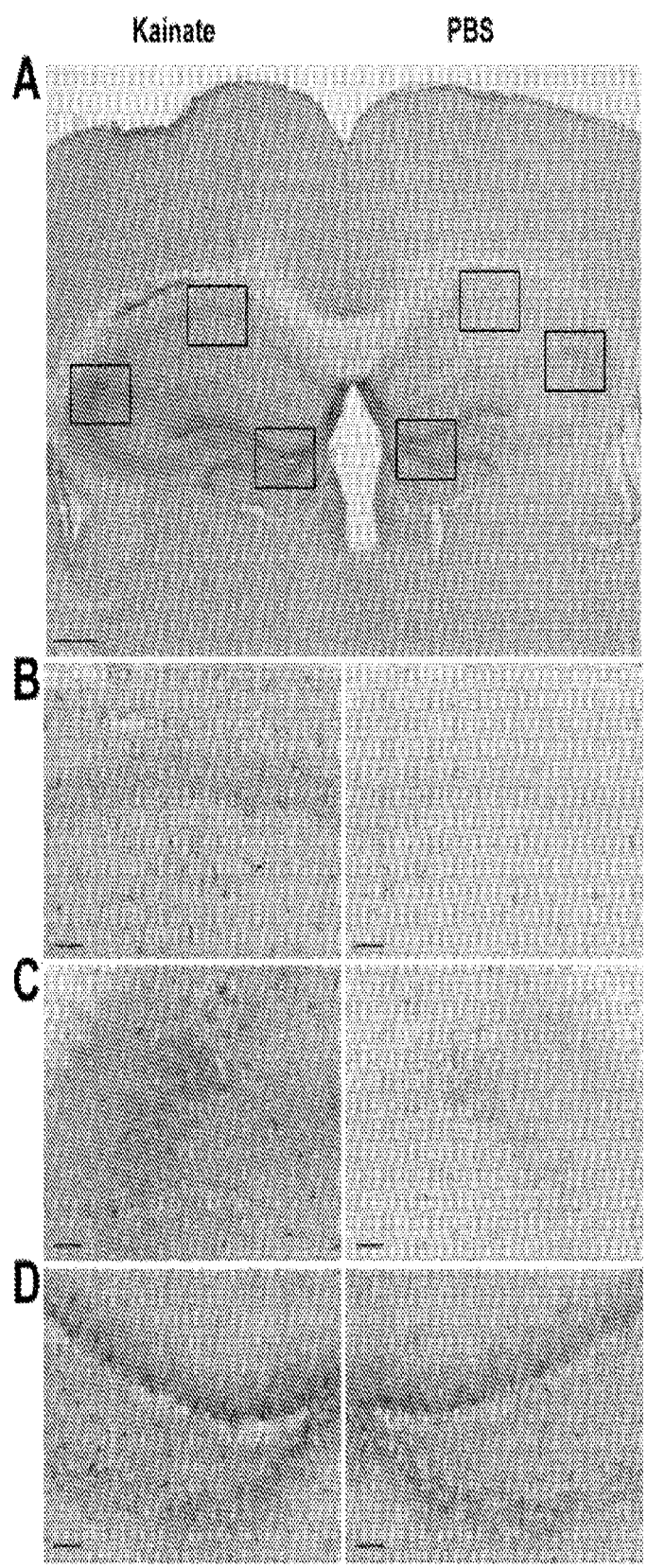

FIG. 9 illustrates that the c-Fms reporter gene is upregulated after stereotaxic kainate injury, as further detailed in Example 4. c-Fms reporter mice (MAFIA, 2 month of age) were lesioned with a unilateral stereotaxic injection of kainic acid (50 ng, left hemibrain) or PBS (right hemibrain). Mice were sacrificed 6 h later and brain sections were analyzed for reporter gene expression by EGFP immunostaining. (A) A representative mouse coronal brain section shows upregulation of the reporter gene in the kainate lesioned side (left hemibrain). (B-D) Rectangles indicate the areas of CA1 (B), CA3 (C) and dentate gyrus (D) shown at higher magnification. Scale bars=400 μm in (A), =50 μm in (B-D).

Figure 10:
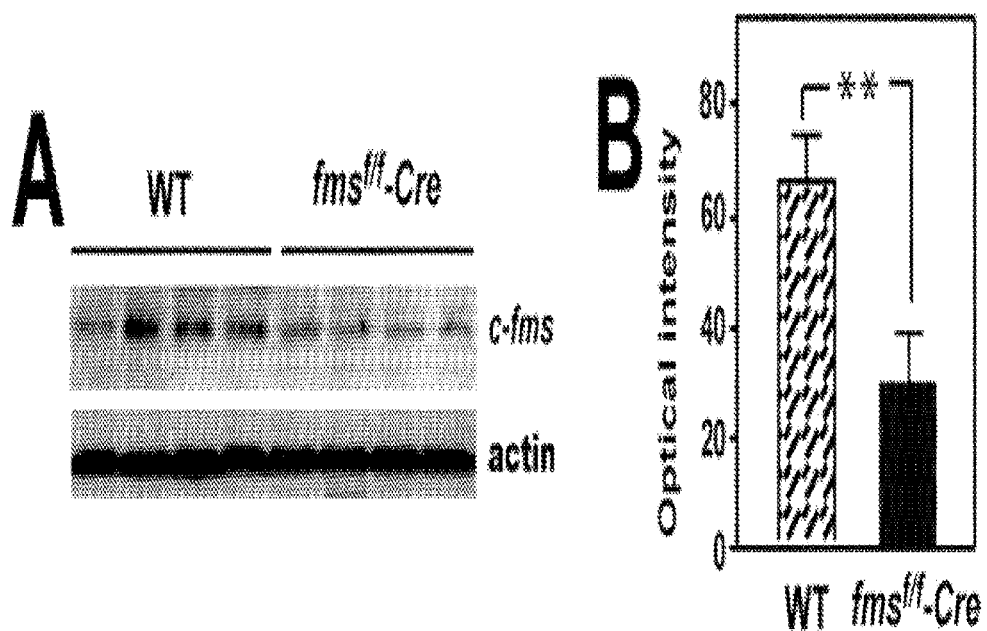

FIG. 10 illustrates the deletion of the c-Fms receptor in c-fms$^{f/f}$-cre mutant mice, as further detailed in Example 5. Wildtype (WT) or c-fms$^{f/f}$-cre littermate mice (2 month of age) were lesioned with kainic acid (20 mg/kg, subcutaneous injection) and sacrificed 6 h later. Hippocampi were isolated and subjected to Western blot analysis. (A) Immunoblotting of c-Fms levels in hippocampal homogenates from wildtype and mutant mice. Actin served as loading control. (B) Quantification of c-Fms levels determined by immunoblotting. **, P<0.01 by t test.

Figure 11:
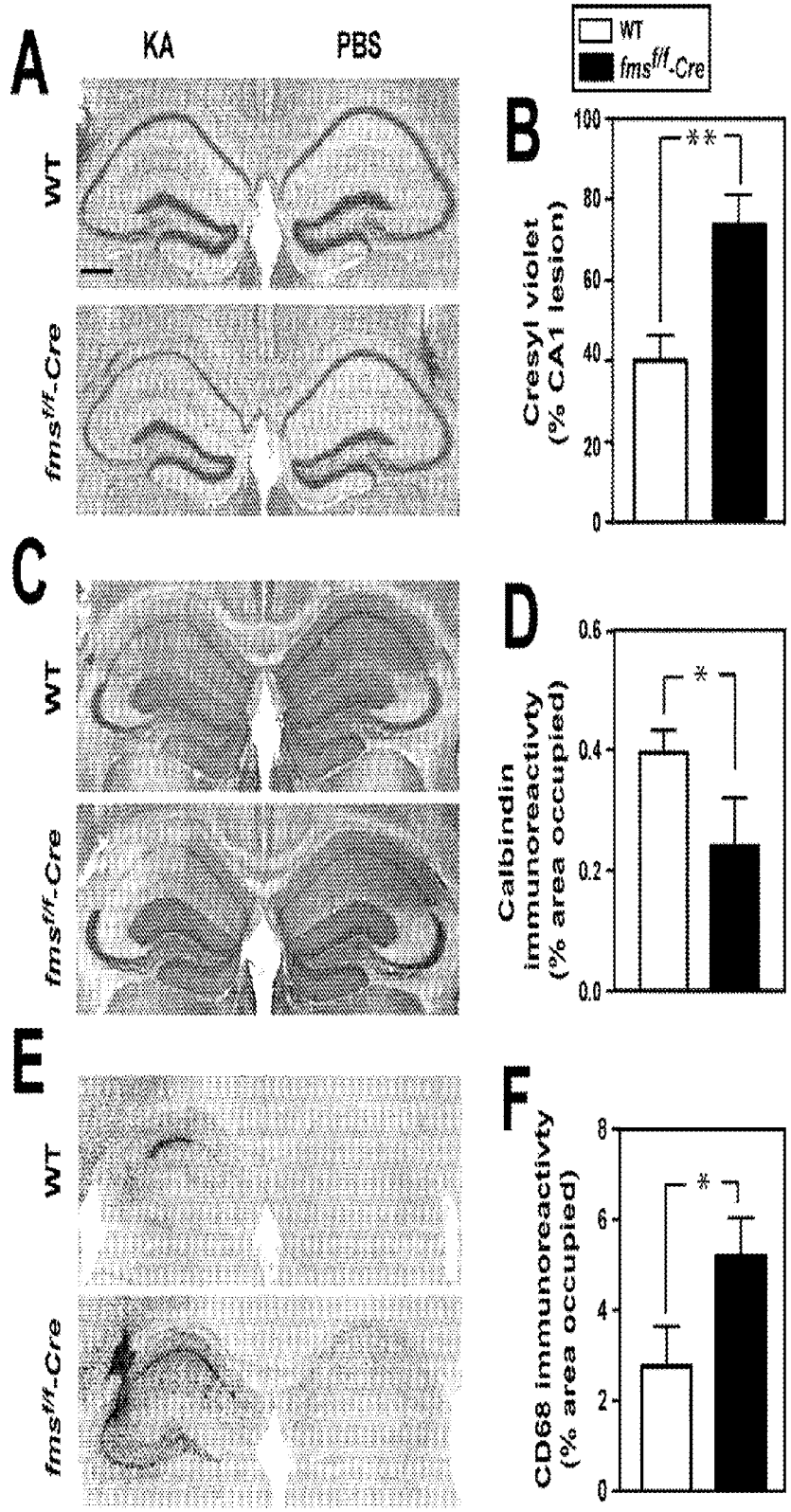

FIG. 11 illustrates that deletion of c-Fms in neurons increases susceptibility to kainic acid-induced excitotoxic injury, as further detailed in Example 5. c-fms$^{f/f}$-cre mice and their wildtype littermates (2 month of age) were lesioned with a unilateral stereotaxic injection of kainic acid (50 ng) or PBS into the hippocampus. Mice were sacrificed 5 days later and brain sections were analyzed for neuronal injury by cresyl violet staining (A, B), calbindin immunostaining (C, D) and CD68 immunostaining (microglial activation, E, F). In (A, C, E), mice from the wildtype (top panel) and mutant group (bottom panel) are shown. Scale bar=200 µm. Bars in (B, D, F) are mean±SEM (n=3-4 mice/group) from one out of two experiments. * $P<0.05$, ** $P<0.01$ compared with wildtype by student t test.

Figure 12:
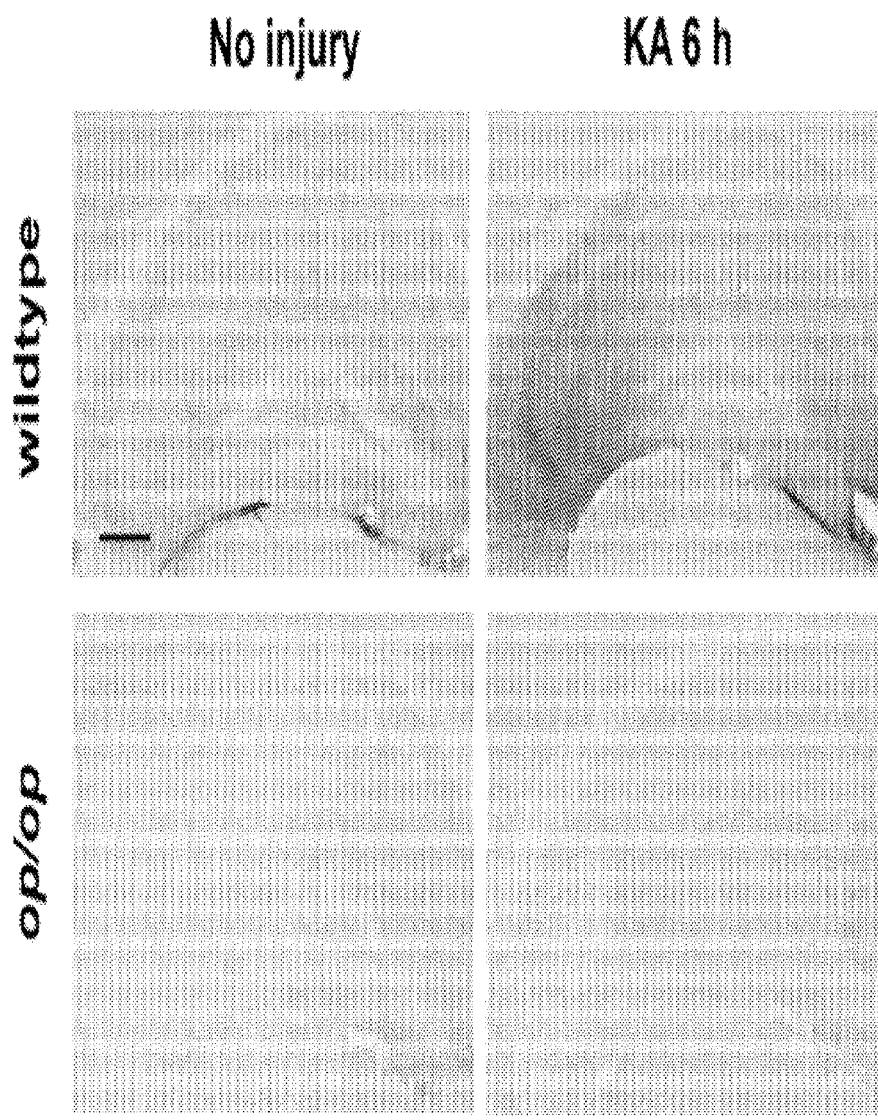

FIG. 12 illustrates that M-CSF immunoreactivity is absent in op/op mice, as further detailed in Example 6. Wildtype FVB/N mice (2 month of age, top panels) or op/op mice (bottom panels) were lesioned with kainic acid (20 mg/kg, subcutaneous injection) and sacrificed 6 h later. Brain sections were immunostained with an antibody against M-CSF. Representative mice shown from left to right were controls (no injury), kainic acid lesioned and sacrificed at 6 h. Scale bar=200 µm.

Figure 13:
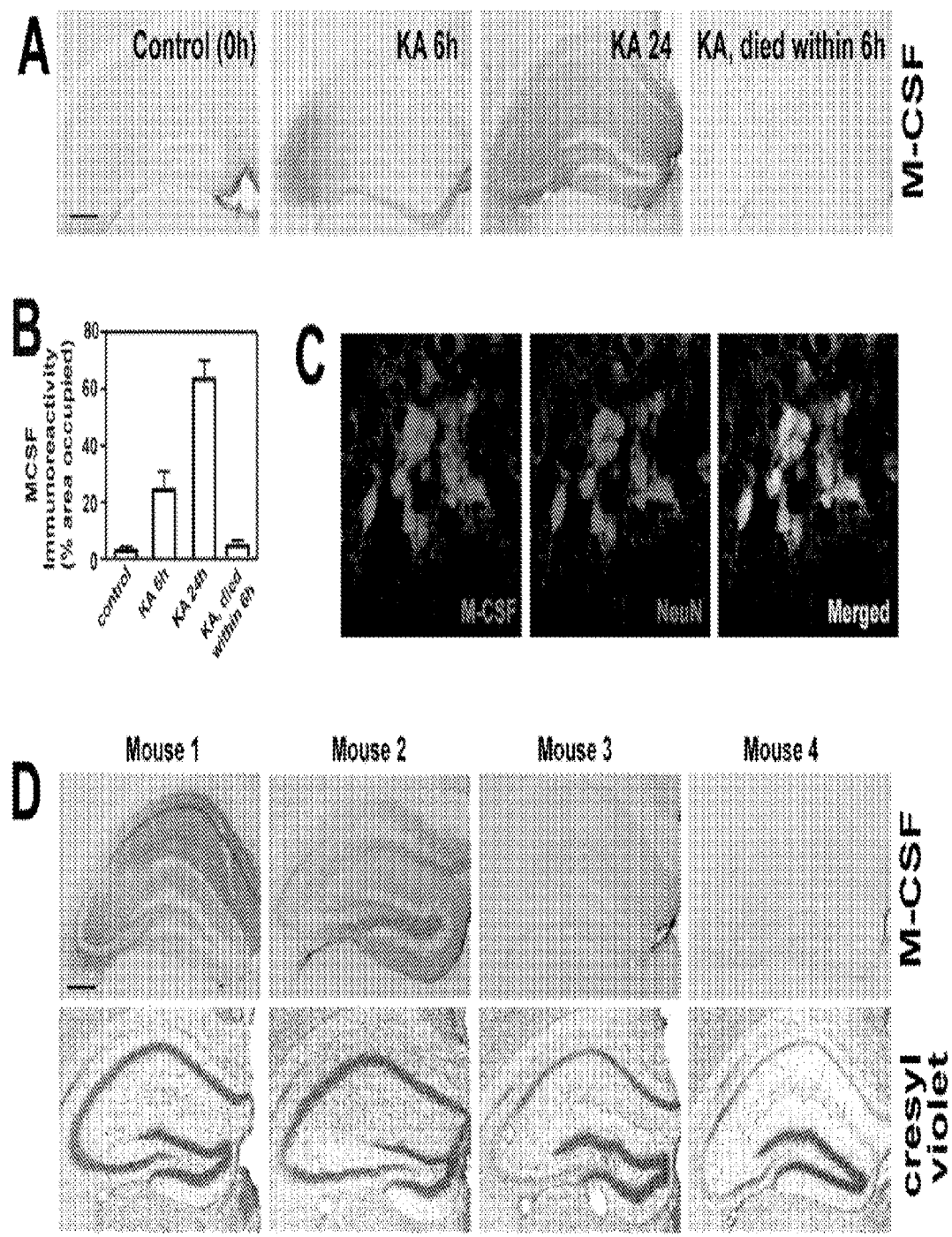

FIG. 13 illustrates that endogenous M-CSF is upregulated in neurons after excitotoxic brain injury, as further detailed in Example 6. Wildtype FVB/N mice (2 month of age) were lesioned with kainic acid (20 mg/kg, subcutaneous injection) and sacrificed 6 h, 1 day, and 3 days later. Brain sections were immunostained with an antibody against M-CSF. (A) Representative mice shown from left to right were controls (no injury), kainic acid lesioned and sacrificed at 6 h, kainic acid lesioned and sacrificed at 24 h, and kainic acid lesioned and died within 6 h. (B) Quantification of M-CSF immunoreactivity in the hippocampus after kainate injury. (C) Co-localization of M-CSF (green) and neuronal marker NeuN (red) after kainic acid lesion. (D) Illustrations of the different degrees of injury assessed by cresyl violet staining caused by kainic acid 3 days after injection and the inverse correlation with M-CSF immunoreactivity. Scale bar=200 µm in (A, C), =20 µm in (B).

Figure 14:
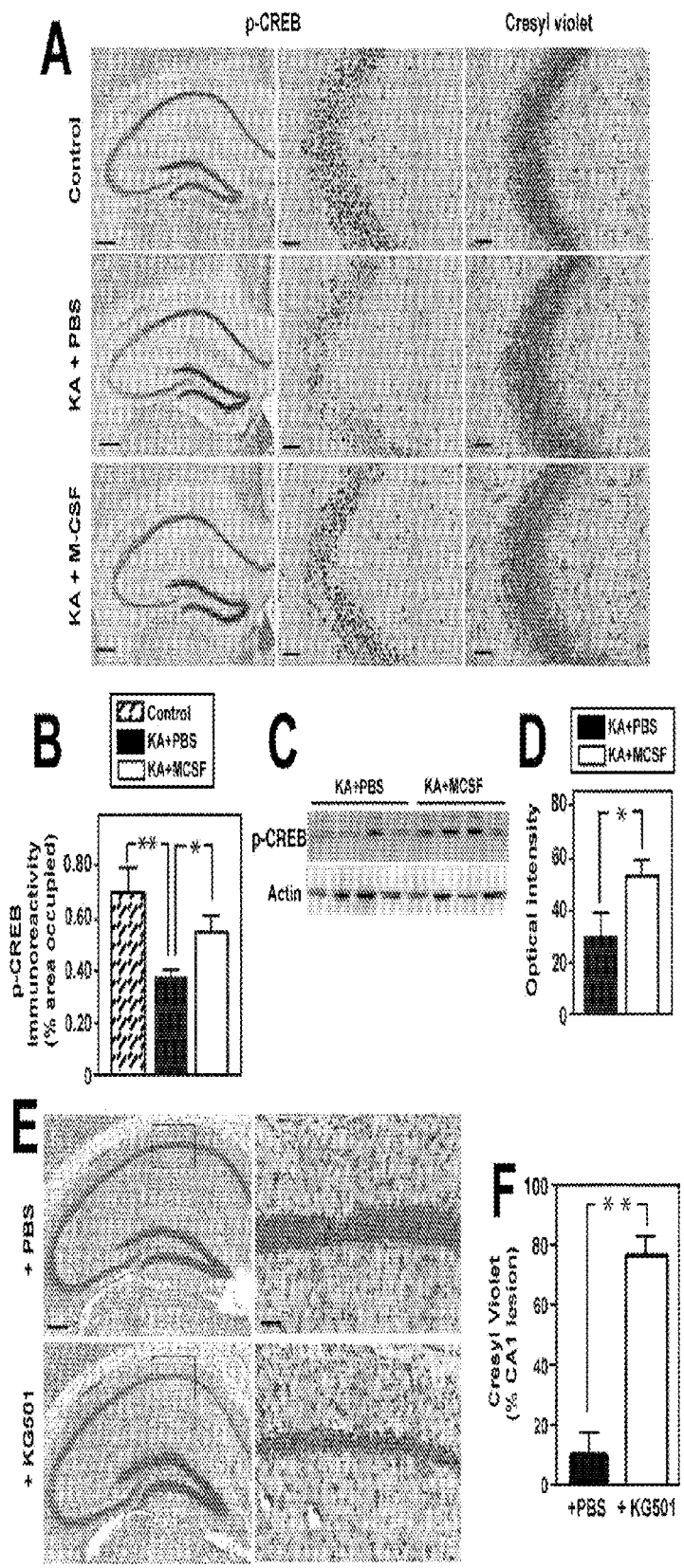

FIG. 14 illustrates that M-CSF activates CREB pathway, as further detailed in Example 7. (A-D) Wildtype FVB/N mice (n=4-6 per group, 2 months of age) were lesioned with kainic acid (20 mg/kg, subcutaneous injection) and treated with M-CSF (24 h before kainic acid) or PBS as control. Mice were sacrificed 6 h after kainic acid injection. One hemibrain was fixed for immunohistochemistry with an antibody against p-CREB (A) (left and middle panels) and p-CREB immunoreactivity was quantified as percentage of area occupied (B). The opposite hippocampi were isolated and subjected to Western blot analysis for p-CREB (C, D) (n=4 mice/group). (E, F) Wildtype FVB/N mice were each stereotaxically implanted with an ALZET brain infusion kit connected to a mini-osmotic pump filled with KG501 or DMSO (control). Two days later, M-CSF (2 h before KA) and KA were injected systemically. Mice were sacrificed 5 days later and brain sections were analyzed for neuronal injury by cresyl violet staining (n=5 mice/group). Scale bars in (A), =200 µm in the left panel, and 50 µm in middle and right panels; in (E), =200 µm in the left panel, and 50 µm in the right panel. *, $P<0.05$; **, $P<0.01$ compared with KA+PBS by ANOVA and Bonferroni post-hoc test (B) or t test (D, F).

Figure 15:
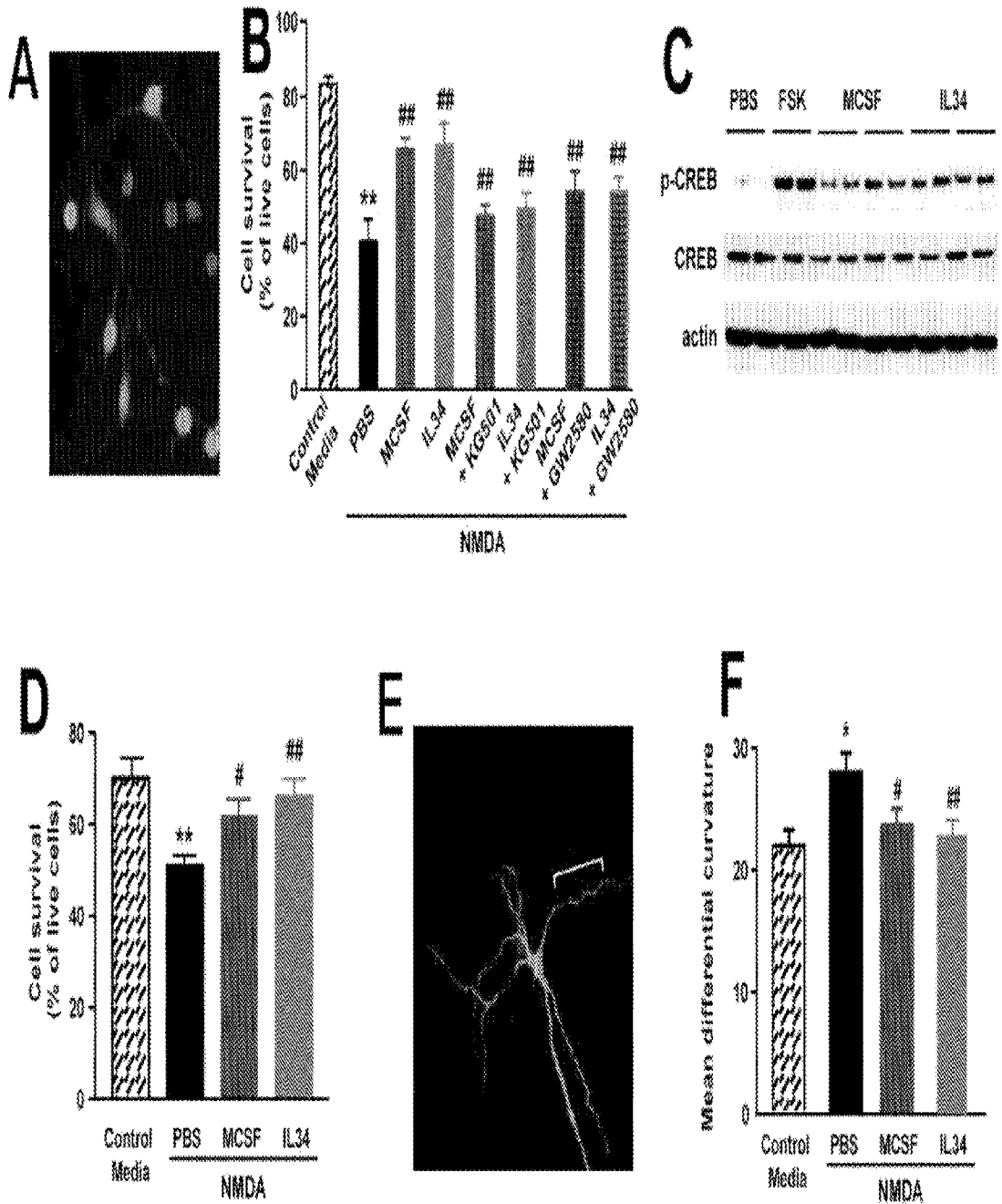

FIG. 15 illustrates that recombinant M-CSF and IL-34 inhibit excitotoxic injury and activate CREB pathway in vitro, as further detailed in Example 8. (A-B) B103 cells were incubated with NMDA for 24 h. MCSF (1 ng/ml) and IL-34 (1 ng/ml) were added 2 h before NMDA. For inhibitor experiments, KG501 (25 µM) or GW2580 (10 µM) was co-incubated with M-CSF or IL-34. Following incubations live and dead cells were assessed with calcein-acetoxymethylester (CAM) and SYTOX Orange (Invitrogen), respectively. Under a fluorescence microscope, the live cells showed green color and the nuclei of dead cells exhibited orange fluorescence (shown in red) (A). Cell survival was expressed as the percentage of live cells over total number of the cells (B). **, $P<0.05$ vs control media, ##, $P<0.01$ vs NMDA+PBS; ANOVA, Tukey's post-hoc test. (C) B103 cells were exposed to forskolin (FSK, 10 µM), IL-34 (1 or 100 ng/ml) and MCSF (1 or 100 ng/ml) for 30 min. The cells were lysed and subjected to Western blot analysis for p-CREB. Forskolin is commonly used to raise levels of cyclic AMP (cAMP) and used as positive control. Note that forskolin exposure caused a prominent increase in CREB phosphorylation. Exposure to IL-34 and M-CSF caused a similar increase in CREB phosphorylation. (D-F). M-CSF and IL-34 prevent NMDA-induced cell death and neurite dystrophy in primary neuronal culture. Primary hippocampal neurons were isolated from 16 days old CF1 mouse embryos and were aged for 6-7 days or 21-22 days, then challenged with 100 µM NMDA in the presence and absence of M-CSF or IL-34 (both at 10 ng/ml), and assayed for neurotoxicity (D) or neuritic dystrophy (E-F), respectively. For the neurotoxicity assay, live and dead cells were counted according to their morphologies determined by phase-contrast microscopy. Results were expressed as % of live cells. For the neuritic dystrophy assay, cultures were fixed and immunostained for MAP-2 to visualize dendrites. Dystrophic neurites show increased tortuosity, exhibiting multiple abrupt turns (brackets) (E). Mean differential curvature analysis in randomly selected fields demonstrated that NMDA induced a significant increase in neurite curvature, which was prevented by M-CSF and IL-34 (n=5 fields/well) (F). Dystrophic curvature analysis was measured by blinded observers. *, $P<0.05$, vs culture media; #, $P<0.05$, ##, $P<0.01$, vs NMDA+PBS; ANOVA, Tukey's post-hoc test.

Figure 16:
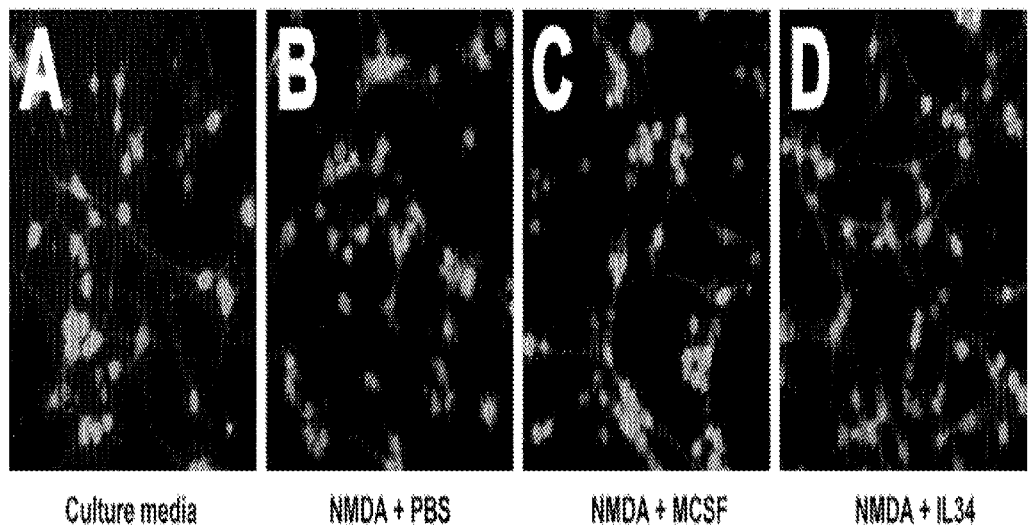
Figure 16:
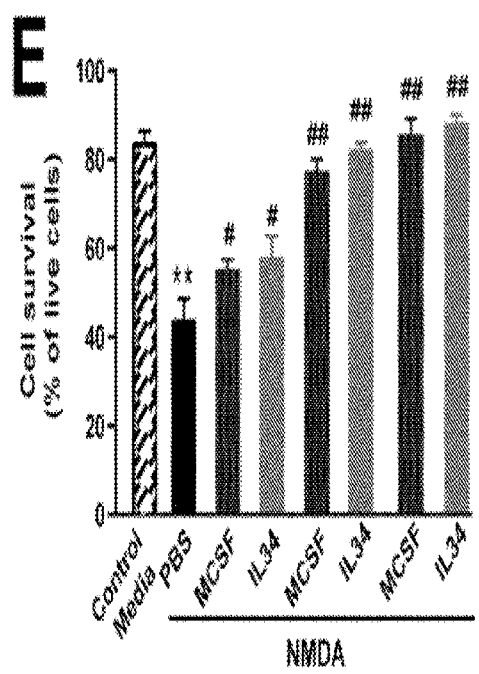

FIG. 16 illustrates that M-CSF as well as IL-34 inhibit NMDA-induced cell death in B103 cells, as further detailed in Example 8. B 103 neuroblastoma cells were incubated with NMDA for 24 hrs. M-CSF and IL-34 were added 2 hrs before NMDA. Following incubations live and dead cells were assessed with calcein-acetoxymethylester (CAM) and SYTOX Orange (Invitrogen), respectively. Under a fluorescence microscope, the live cells showed green color and the nuclei of dead cells exhibited orange fluorescence (shown in red). Representative images showing increased cell death after NMDA exposure (100 µM, B) compared with control media (A), and the reduction by the treatment of M-CSF (C) and IL-34 (D). Cell survival was expressed as the percentage of live cells over total number of the cells (E). Concentrations used, 1, 10 and 100 ng/ml, from left to right, for both M-CSF and IL-34. **, $P<0.01$ vs culture media; #, $P<0.05$, ##, $P<0.01$ vs NMDA+PBS; ANOVA, Tukey's post-hoc test.

Figure 17:
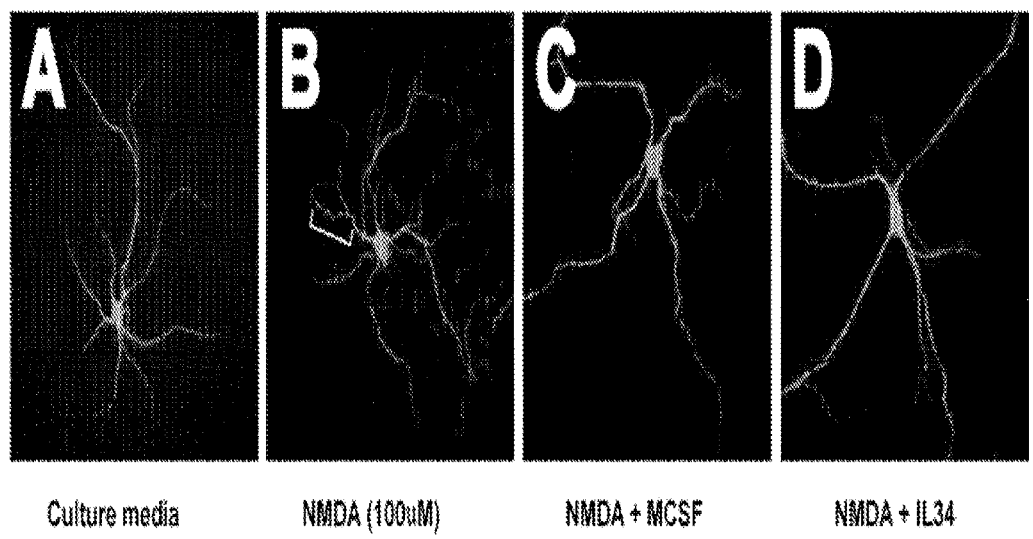
Figure 17:
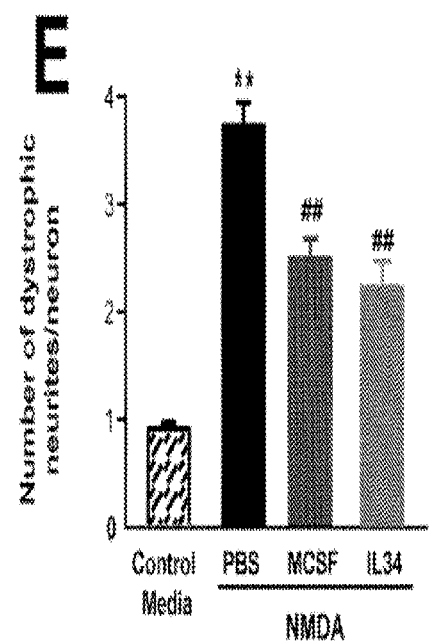

FIG. 17 illustrates that M-CSF and IL-34 prevent NMDA-induced neurite dystrophy, as further detailed in Example 8. Hippocampal neurons (21-22 DIV) were exposed to culture medium (A), 100 µM NMDA (B); 100 µM NMDA+10 ng/ml M-CSF (C), or 100 µM NMDA+10 ng/ml IL-34 (D). After 48 hrs, cultures were fixed and immunostained for MAP-2 to visualize dendrites. Note that NMDA exposure significantly increased tortuosity, exhibiting multiple abrupt turns (brackets) (B), and was markedly reduced by M-CSF and IL-34 (C, D). (E) Average numbers of dystrophic neurites per neuron (n=10 fields/well). Dystrophic neurites were defined as neurites exhibiting multiple abrupt turns (tortuosity) and were measured by blinded observers. **, P<0.01 vs culture media; ##, P<0.01 vs NMDA+PBS; ANOVA, Tukey's post-hoc test.

Figure 18:
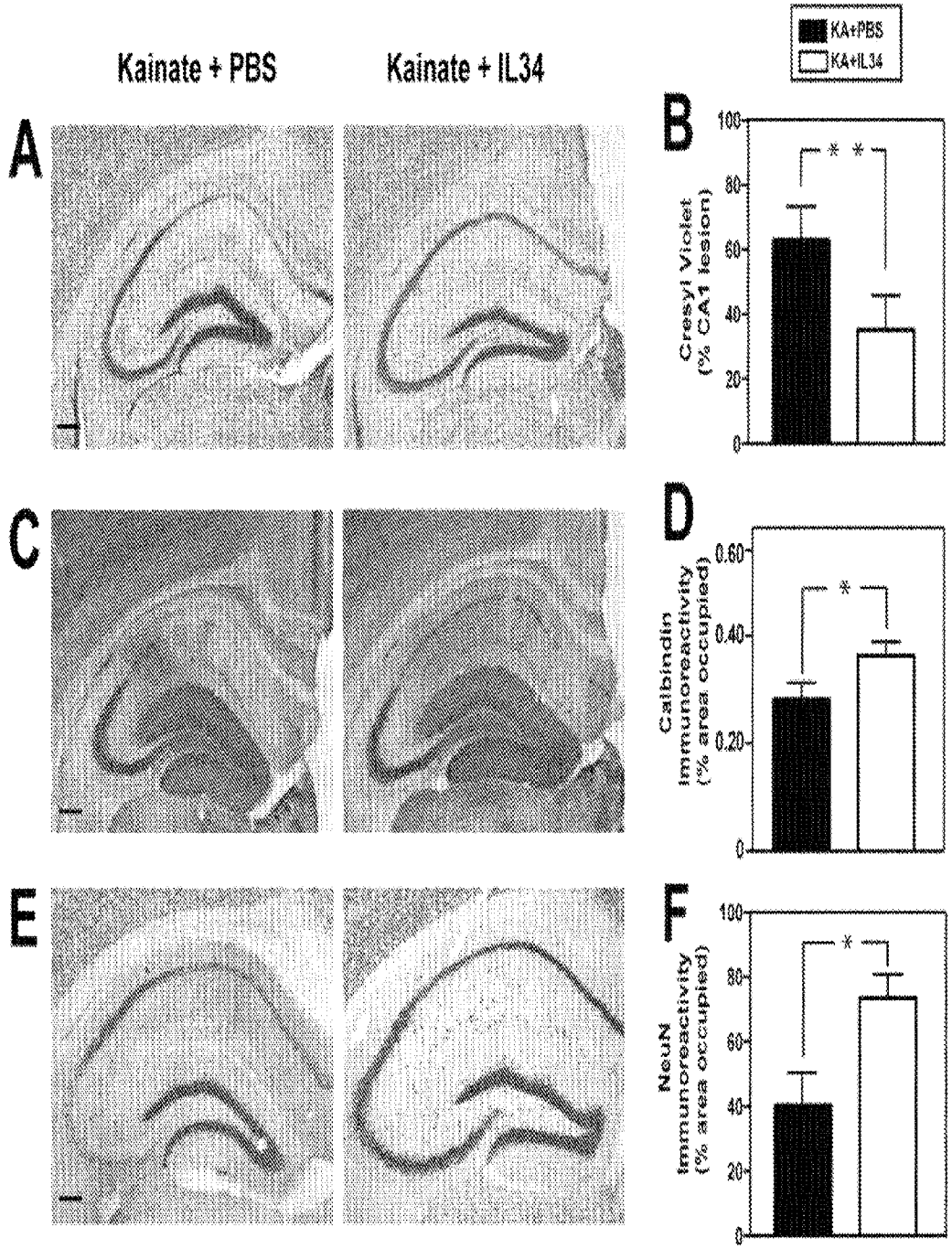

FIG. 18 illustrates that systemic IL-34 attenuates kainic acid-induced neurodegeneration, as further detailed in Example 9. Two-month-old FVB/N mice were lesioned with kainic acid (20 mg/kg, subcutaneous injection) and sacrificed 5 days later. IL-34 (100 µg/kg) was injected intraperitoneally once 2 h before kainic acid. Kainic acid-induced neuronal injury was assessed by cresyl violet staining (A, B), calbindin (C, D) and NeuN (E, F) immunostaining. Representative images are shown from hippocampi of mice treated with PBS (left) or IL-34 (right). Scale bar=200 µm. Bars in (B, D, and F) are mean±SEM (n=4 mice/group). *, P<0.05; **, P<0.01, student t test.

Figure 19:
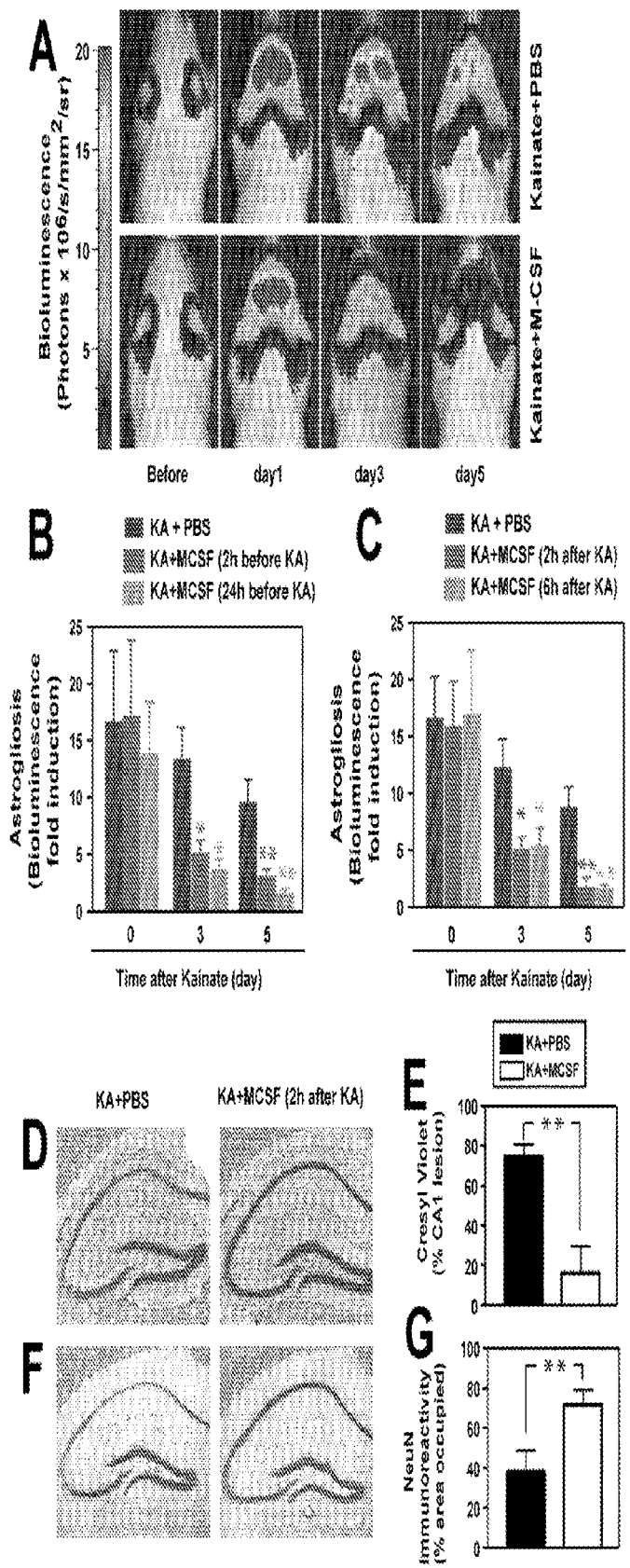

FIG. 19 illustrates that the systemic administration of M-CSF inhibits kainic acid-induced reporter gene activity, as further detailed in Example 10. (A-C) GFAP-luc mice (2 month of age) were lesioned with kainic acid (20 mg/kg) and bioluminescence was recorded at indicated time points in each mouse. Representative images showing increased bioluminescence signals over the brain after kainic acid injury (top panel) and the reduction by M-CSF treatment 24 h before kainic acid (bottom panel) (A). Time course of bioluminescence induction. Bioluminescence is expressed as fold induction over baseline in the mice treated with M-CSF at 2 or 24 h before kainic acid (B) or at 2 or 6 h after kainic acid (C). Baseline was measured 1 day before kainic acid administration for each mouse. Bars are mean±SEM (n=4-7 mice). Recombinant human M-CSF was injected intraperitoneally at 800 µg/kg body weight, unless otherwise specified. *, P<0.05; , P<0.01 compared with KA+PBS by ANOVA and Bonferroni post-hoc test. (D-G) After bioluminescence imaging GFAP-luc mice were sacrificed (5 d after kainate). Excitotoxic injury was assessed by cresyl violet staining (D, E) and NeuN immunostaining (F, G). Representative images are shown from hippocampi of mice treated with PBS (left) or M-CSF (administered 2 h after kainate, right). Scale bar=200 µm. Bars in (D and F) are mean±SEM (n=3-4 mice/group). , P<0.01, student t test.

DETAILED DESCRIPTION

Before describing detailed embodiments of the invention, it will be useful to set forth definitions that are utilized in describing the present invention.

Definitions

The practice of the present invention may employ conventional techniques of neurochemistry, neuroscience, immunohistochemistry and molecular biology, which are within the capabilities of a person of ordinary skill in the art. Such techniques are fully explained in the literature. For definitions, terms of art and standard methods known in the art, see, for example, Sambrook and Russell "Molecular Cloning: A Laboratory Manual", Cold Spring Harbor Laboratory Press (2001); 'Current Protocols in Molecular Biology'; 'Current Protocols in Immunology'; Stanley ER "Colony stimulating factor-1", The cytokine handbook, 1994, Academic Press. Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise.

The term "macrophage colony stimulating factor receptor agonists", as used herein, relates to biologically active, recombinant, isolated peptides and proteins, including their biologically active fragments, peptidomimetics and small molecules that are capable of stimulating the Macrophage colony stimulating factor receptor, M-CSFR or c-fms. M-CSFR agonists are also referred to as c-fms ligands herein.

The terms "M-CSF", "macrophage colony stimulating factor", "CSF-1", "CSF1", "colony stimulating factor1" and "colony stimulating factor-1" are used interchangeably herein.

The term "subject", as used herein, refers to an animal, preferably a mammal, including mouse, rabbit, dog, cat, guinea pig, goat, cow, horse, pig, sheep, monkey, primate, ape, and human.

The term "cognitive function", as used herein, refers to a subject's ability to store and retrieve memories, learn, communicate and/or function independently.

The term "therapeutic effect", as used herein, refers to a consequence of treatment that might intend either to bring remedy to an injury that already occurred or to prevent an injury before it occurs. A therapeutic effect may include, directly or indirectly, the reduction of neuronal damage and the stimulation of neuronal repair following acute or chronic injury of nerve cells. A therapeutic effect may also include, directly or indirectly, the arrest, reduction, or elimination of the progression of neuronal cell death following acute or chronic injury of nerve cells. Furthermore, a therapeutic effect may include, directly or indirectly, the prevention or reduction of neuronal damage prior to acute or chronic injury of nerve cells.

The term "therapeutically effective amount" of a macrophage colony stimulating factor receptor agonist is an amount that is sufficient to provide a therapeutic effect in a mammal, including a human. Naturally, dosage levels of the particular macrophage colony stimulating factor receptor agonist employed to provide a therapeutically effective amount vary in dependence of the type of injury, the age, the weight, the gender, the medical condition of the mammal/human, the severity of the condition, the route of administration, and the particular macrophage colony stimulating factor receptor agonist employed. Therapeutically effective amounts of a macrophage colony stimulating factor receptor agonist, as described herein, can be estimated initially from cell culture and animal models. For example, $IC_{50}$ values determined in cell culture methods can serve as a starting point in animal models, while $IC_{50}$ values determined in animal models can be used to find a therapeutically effective dose in humans.

The term "recombinant", as used herein, relates to a protein or polypeptide that is obtained by expression of a recombinant polynucleotide.

The terms "isolated" and "purified" relate to molecules that have been manipulated to exist in a higher concentration or purer form than naturally occurring.

The term "pharmaceutical composition", as used herein, refers to a mixture of at least one macrophage colony stimulating factor receptor agonist with chemical components such as diluents or carriers that do not cause unacceptable adverse side effects and that do not prevent the macrophage colony stimulating factor receptor agonist(s) from exerting a therapeutic effect. A pharmaceutical composition serves to facilitate the administration of the macrophage colony stimulating factor receptor agonist(s).

Neuronal Viability, Repair and Protection; Neuronal Death

The term "attenuating neuronal damage", as used herein, refers to the macrophage colony stimulating factor receptor agonists' ability to reduce neuronal death and to protect neurons of the central nervous system, in vitro as well as in vivo, from neuronal death, both in quality and quantity, when compared to a negative control compound or vehicle that does not attenuate neuronal damage.

The term "stimulating neuronal repair", as used herein, refers to the macrophage colony stimulating factor receptor agonists' ability to restore neuronal viability and function following a neuronal injury or insult. Neuronal viability is maintained through a complex network of signaling pathways that can be disturbed in response to a wide variety of cellular stress.

Neuronal insults due to traumatic brain injury, cerebral ischemia, glucose deprivation or degenerative disease cause an upregulation in the expression of neuroprotective factors and their receptors in an array of cells that are involved in the neuronal repair process, including astrocytes and microglia, macrophages, mastcells and other invading inflammatory cells, T cells and certain neurons (Sofroniew et al., 2001).

The mitogen-activated protein (MAP) kinases and phosphatidylinositol-3 kinase (PI3K) are serine/threonine protein kinases that play critical roles in neuronal growth, differentiation and survival. Activation of the ERK or p42/p44 MAP kinase members of the MAP kinase family and activation of the PI3K Akt signaling pathway promote cell survival, while stress-activated protein kinases (SAPK's), c-Jun N-terminal kinases (JNK's) and the p38 MAP kinase (p38 MAPK), which are also members of the MAP kinase family, facilitate cell death (Morrison et al., 2002).

Many neuroprotective factors such as nerve growth factor (NGF), brain-derived neurotrophic factor (BDNF), neurotrophin-3 (NT-3), neurotrophin-4 (NT-4), novel neurotrophin-1 (NNT-1) or insulin-like growth factor 1 (IGF-1) exert their actions through a particular signaling pathway. Nerve growth factor (NGF) is critical for the survival and maintenance of sympathetic and sensory neurons. Upon release from its target neurons, NGF binds to and activates its high affinity receptor TrkA on the target neurons and is internalized into the responsive neurons; NGF might also act through the p75 receptor (aka low-affinity nerve growth factor receptor, LNGFR). BDNF is expressed in the brain and in some peripheral tissues and supports the survival of existing neurons as well as stimulates neurogenesis both in the central and peripheral nervous system. It exerts its action through the TrkB and p75 receptors. NT-3 aids in the survival of existing neurons and supports neurogenesis both in the peripheral and central nervous system. It exerts its action through the TrkB, TrkC and p75 receptors. NT-4 has similar functions like NT-3 and activates primarily the TrkB receptor. IGF-1, in its function as neurotrophic factor, helps in the survival of neurons and acts through the stimulation of the IGF-1 receptor. p75 (LNGFR) belongs to a family of receptors that includes CD27, CD30, CD40, OX40, Fas (CD95), and the tumor necrosis factor receptors (TNF-R). All these family members are able to control cell viability through the regulation of apoptosis (Sofroniew et al., 2001). The Trk receptor family (TrkA, TrkB and TrkC) as well as the IGF-1 receptor are receptor tyrosine kinases and act via the PI3K Akt signaling pathway, which involves activation of the cAMP responsive elements binding protein, CREB.

CREB belongs to a family of proteins that function as transcription factors. It is expressed in all cells of the central nervous system and is assumed to play a key role in the protection of neurons and in neuronal survival following neuronal damage (Walton & Dragunow, 2000). CREB activation has been implicated in the resistance of neuronal cells to various injuries and insults, but there is now evidence that the Akt signaling pathway could lead to CREB activation (Morrison et al., 2002). CREB signaling also appears to play a major role in mediating M-CSF's biological effects in macrophages (Casals-Casas et al., 2009). Furthermore, kainic acid injury was shown to selectively decrease phosphorylation of CREB (phospho-CREB) in vulnerable regions (Ferrer et al., 2002).

Neuronal cell death as a consequence of apoptotic or necrotic events can be caused in acute and chronic ways through neuronal damage and neuroinflammation. Acute neuronal injury and acute neurodegeneration can be caused by a traumatic brain injury due to a sudden, violent insult, by cerebral ischemia due to restricted blood supply, glucose deprivation, oxidative stress through free radicals or spinal cord injury. Neurodegenerative diseases of the central nervous system (CNS) such as Alzheimer's disease, Parkinson's disease, Amyotrophic Lateral Sclerosis and Huntington's disease lead to chronic neurodegeneration. Excitotoxic injury (excitatory amino acid neurotoxic injury) following overstimulation of the glutamate receptors, the NMDA receptor or the AMPA receptor, by the neurotransmitter glutamate or molecules with a similar effect (so-called excitotoxins), such as N-methyl D-aspartate (NMDA) or kainic acid, may be involved in both acute and chronic neurodegenerative events.

Alzheimer's disease is characterized by progressive memory loss and cognitive dysfunction; neuropathological changes that are assessed post-mortem include amyloid plaques, neurofibrillary tangles, neuroinflammation and microvascular changes (Querfurth & LaFerla, 2010).

Parkinson's disease is a degenerative disorder of the central nervous system that primarily impairs motor skills and speech. These symptoms result from decreased stimulation of the motor cortex due to insufficient production of dopamine in dopaminergic neurons of the brain. It is assumed that the presence of Lewy bodies contributes to the gradual death of brain cells and tissue.

Huntington's disease is a progressive, neurodegenerative, genetically based disorder that results from brain damage caused by aggregats of misfolded huntingtin protein and that affects muscle coordination and cognitive functions, typically from middle age on.

Amyotrophic Lateral Sclerosis is characterized by the degeneration of upper and lower motor neurons with the ultimate disability to initiate and control voluntary movement.

Dosages, Dosing Regimens, Formulations and Administration of Macrophage Colony Stimulating Factor Receptor Agonists The dosage and dosing regimen for the administration of a macrophage colony stimulating factor receptor agonist for attenuating neuronal damage and for stimulating neuronal repair, as provided herein, is selected by one of ordinary skill in the art, in view of a variety of factors including, but not limited to, age, weight, gender, and medical condition of the subject, the severity of the neuronal damage that is experienced, the route of administration (oral, systemic, local), the dosage form employed, and may be determined empirically using testing protocols, that are known in the art, or by extrapolation from in vivo or in vitro tests or diagnostic data.

The dosage and dosing regimen for the administration of a macrophage colony stimulating factor receptor agonist, as provided herein, is also influenced by toxicity in relation to therapeutic efficacy. Toxicity and therapeutic efficacy can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Molecules that exhibit large therapeutic indices are generally preferred.

The effective dose of a macrophage colony stimulating factor receptor agonist, can, for example, be less than 50 mg/kg of subject body mass, less than 40 mg/kg, less than 30 mg/kg, less than 20 mg/kg, less than 10 mg/kg, less than 5 mg/kg, less than 3 mg/kg, less than 1 mg/kg, less than 0.3 mg/kg, less than 0.1 mg/kg, less than 0.05 mg/kg, less than 0.025 mg/kg, or less than 0.01 mg/kg. Effective doses of a macrophage colony stimulating factor receptor agonist, administered to a subject as provided in the methods herein can, for example, be between about 0.001 mg/kg to about 50 mg/kg. In certain embodiments, the effective dose is in the range of, for example, 0.005 mg/kg to 10 mg/kg, from 0.01 mg/kg to 2 mg/kg, or from 0.05 mg/kg to 0.5 mg/kg. In various embodiments, an effective dose is less than 1 g, less than 500 mg, less than 250 mg, less than 100 mg, less than 50 mg, less than 25 mg, less than 10 mg, less than 5 mg, less than 1 mg, less than 0.5 mg, or less than 0.25 mg per dose, which dose may be administered once, twice, three times, or four or more times per day. In certain embodiments, an effective dose can be in the range of, for example, from 0.1 mg to 1.25 g, from 1 mg to 250 mg, or from 2.5 mg to 1000 mg per dose. The daily dose can be in the range of, for example, from 0.5 mg to 5 g, from 1 mg to 1 g, or from 3 mg to 300 mg.

In some embodiments, the dosing regimen is maintained for at least one day, at least two days, at least about one week, at least about two weeks, at least about three weeks, at least about one month, or longer. In some embodiments, an intermittent dosing regimen is used, i.e., once a month, once every other week, once every other day, once per week, twice per week, and the like. In some embodiments, the compound is administered at least once daily for at least five consecutive days.

Routes of administration of macrophage colony stimulating factor receptor agonists or pharmaceutical compositions containing macrophage colony stimulating factor receptor agonists may include, but are not limited to, oral, nasal and topical administration and intramuscular, subcutaneous, intravenous, intraperitoneal or intracerebral injections. The macrophage colony stimulating factor receptor agonists or pharmaceutical compositions containing macrophage colony stimulating factor receptor agonists may also be administered locally via an injection or in a targeted delivery system.

The macrophage colony stimulating factor receptor agonist may be administered in a single daily dose, or the total daily dose may be administered in divided doses, two, three, or more times per day. Optionally, in order to reach a steady-state concentration in the brain quickly, an intravenous bolus injection of the macrophage colony stimulating factor receptor agonist can be administered followed by an intravenous infusion of the macrophage colony stimulating factor receptor agonist.

The macrophage colony stimulating factor receptor agonist can be administered to the subject as a pharmaceutical composition that includes a therapeutically effective amount of the macrophage colony stimulating factor receptor agonist in a pharmaceutically acceptable vehicle. It can be incorporated into a variety of formulations for therapeutic administration by combination with appropriate pharmaceutically acceptable carriers or diluents, and may be formulated into preparations in solid, semi-solid, liquid, or gaseous forms, such as tablets, capsules, powders, granules, ointments, solutions, suppositories, injections, inhalants, gels, microspheres, and aerosols.

In some embodiments, the macrophage colony stimulating factor receptor agonist can be formulated as a delayed release formulation. Suitable pharmaceutical excipients and unit dose architecture for delayed release formulations may include those described in U.S. Pat. Nos. 3,062,720 and 3,247,066. In other embodiments, the macrophage colony stimulating factor receptor agonist can be formulated as a sustained release formulation. Suitable pharmaceutical excipients and unit dose architecture for sustained release formulations include those described in U.S. Pat. Nos. 3,062,720 and 3,247,066. The macrophage colony stimulating factor receptor agonist can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly($\epsilon$-caprolactone) and poly(alkylene oxide) (U.S. 20030068384) to create a sustained release formulation. Such formulations can be used in implants that release an agent over a period of several hours, a day, a few days, a few weeks, or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 9726015, WO 97/04744, and. US20020019446. In such sustained release formulations microparticles of drug are combined with microparticles of polymer. Additional sustained release formulations are described in WO 02/38129, EP 326 151, U.S. Pat. No. 5,236,704, WO 02/30398, WO 98/13029; U.S. 20030064105, U.S. 20030138488A1, U.S. 20030216307A1,U.S. Pat. No. 6,667,060, WO 01/49249, WO 01/49311, WO 01/49249, WO 01/49311, and U.S. Pat. No. 5,877,224.

Pharmaceutical compositions can include, depending on the formulation desired, pharmaceutically-acceptable, nontoxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients, and the like. The compositions can also include additional substances to approximate physiological conditions, such as pH adjusting and buffering agents, toxicity adjusting agents, wetting agents, and detergents. The composition can also include any of a variety of stabilizing agents, such as an antioxidant for example. Tablet formulations can comprise a sweetening agent, a flavoring agent, a coloring agent, a preservative, or some combination of these to provide a pharmaceutically elegant and palatable preparation.

Further guidance regarding formulations that are suitable for various types of administration can be found in Remington's Pharmaceutical Sciences, Mace Publishing Company, Philadelphia, Pa., 20th ed. (2000).

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in-vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Macrophage colony stimulating factor receptor agonists or pharmaceutical compositions containing macrophage colony stimulating factor receptor agonists may be administered to a subject using any convenient means capable of resulting in the desired treatment of neuronal damage and stimulation of neuronal repair. Routes of administration include, but are not limited to, oral, rectal, parenteral, intravenous, intracranial, intraperitoneal, intradermal, transdermal, intrathecal, intranasal, intracheal, intracapillary, subcutaneous, subdermal, topical, intramuscular, injection into the cerebrospinal fluid, injection into the intracavity, or injection directly into the brain. Oral administration can include, for instance, buccal, lingual, or sublingual administration. The macrophage colony stimulating factor receptor agonists may be systemic after administration or may be localized by the use of local administration, intramural administration, or use of an implant that acts to retain the active dose at the site of implantation. For a brief review of methods for drug delivery see Langer, 1990.

Macrophage Colony Stimulating Factor (M-CSF, CSF-1)

Monocytes, macrophages, natural killer (NK) cells, and polymorphonuclear neutrophils (PMN) are part of a subject's innate immune system, which generally acts as the initial defense against foreign cells.

Macrophage colony-stimulating factor (M-CSF), also known as colony-stimulating factor-1 (CSF-1) and initially described as a growth factor of the mononuclear phagocytic lineage, is a secreted cytokine which influences hematopoietic stem cells to differentiate into macrophages or other related cell types and which regulates the survival, proliferation, differentiation, and chemotaxis of cells of the monocyte/macrophage lineage (Hamilton, 2008; Pixley and Stanley, 2004). M-CSF is produced by multiple cell types including monocyte/macrophages, endothelial cells, fibroblasts, and bone marrow stromal cells (Chitu and Stanley, 2006; Hamilton, 2008; Pixley and Stanley, 2004).

Macrophage Colony Stimulating Factor Receptor (M-CSFR)

The biological effects of M-CSF are mediated by a single M-CSF receptor (M-CSFR), a ligand inducible protein tyrosine kinase receptor, which is encoded by the c-fms proto-oncogene (Sherr et al., 1985). M-CSFR is predominantly expressed in mononuclear phagocytes and to a lesser extent in oocytes, trophoblasts, and certain lymphocytes (Chitu and Stanley, 2006; Hamilton, 2008; Pixley and Stanley, 2004). Ligand binding to M-CSFR triggers multiple signal transduction pathways resulting in activation of the protein kinase AKT, the cAMP-response-element-binding protein (CREB) and mitogen-activated protein (MAP) kinase (Hamilton, 1997; Pixley and Stanley, 2004).

Consistent with its role in regulating the monocyte/macrophage lineage, in the central nervous system M-CSFR is expressed in microglia (Raivich et al., 1998) and the presence of M-CSF is crucial for maturation of these cells (Imai and Kohsaka, 2002).

Macrophage Colony Stimulating Factor Receptor Agonists

The present invention provides methods for attenuating neuronal damage and stimulating neuronal repair using compounds that stimulate c-fms (macrophage colony stimulating factor receptor agonists or ligands) following acute or chronic injury of nerve cells of the central nervous system. Macrophage colony stimulating factor receptor agonists stimulate the macrophage colony stimulating factor receptor, M-CSFR or also called c-fms, and may be biologically active, recombinant, isolated peptides and proteins, including their biologically active fragments, peptidomimetics or small molecules. In certain embodiments, such compounds are orally active and can cross the blood brain barrier.

Macrophage colony stimulating factor receptor agonists can be identified experimentally using a variety of in vitro and/or in vivo models. Isolated macrophage colony stimulating factor receptor agonists can be screened for binding to various sites of the purified macrophage colony stimulating factor receptor proteins. Compounds can also be functionally screened for their ability to exert neuroprotective effects using in vitro culture systems. In addition, compounds can be evaluated as potential neuroprotective factors and for treatment or prevention of neuronal death, including cognitive impairment, using animal models (e.g., monkey, rat, or mouse models). Candidate compounds that exert neuroprotective effects may also be identified by known pharmacology, structure analysis, or rational drug design using computer based modeling.

Candidate compounds that exert neuroprotective effects may encompass numerous chemical classes, though typically they are organic molecules, preferably small organic compounds having a molecular weight of more than 50 and less than about 2,500 daltons. They may comprise functional groups necessary for structural interaction with proteins (e.g., hydrogen bonding), and typically include at least an amine, carbonyl, hydroxyl, or carboxyl group. They often comprise cyclical carbon or heterocyclic structures and/or aromatic or polyaromatic structures substituted with one or more functional groups. They may be found among biomolecules including peptides, saccharides, fatty acids, steroids, purines, and pyrimidines, and structural analogs thereof.

Candidate compounds that exert neuroprotective effects can be synthesized or isolated from natural sources (e.g., bacterial, fungal, plant, or animal extracts). The synthesized or isolated candidate compound may be further chemically modified (e.g., acylated, alkylated, esterified, or amidified), or substituents may be added (e.g., aliphatic, alicyclic, aromatic, cyclic, substituted hydrocarbon, halo (especially chloro and fluoro), alkoxy, mercapto, alkylmercapto, nitro, nitroso, sulfoxy, sulfur, oxygen, nitrogen, pyridyl, furanyl, thiophenyl, or imidazolyl substituents) to produce structural analogs, or libraries of structural analogs (see, for example, U.S. Pat. Nos. 5,958,792; 5,807,683; 6,004,617; 6,077,954). Such modification can be random or based on rational design (see, for example, Cho et al., 1998; Sun et al., 1998).

In the working examples human M-CSF protein as well as murine Interleukin-34 protein, both in isolated, purified and/or recombinant form, were utilized as macrophage colony stimulating factor receptor agonists. Such macrophage colony stimulating factor receptor agonists may be administered locally at or near a site of injury within the central nervous system or systemically in a therapeutically effective amount and within a time period following acute or chronic injury that is sufficient to provide a therapeutic effect.

Attenuating Neuronal Damage and Stimulating Neuronal Repair

The present invention provides methods for attenuating neuronal damage and stimulating neuronal repair following acute or chronic injury of nerve cells of the central nervous system. Furthermore, the present invention provides methods for preventing or attenuating neuronal damage prior to chronic injury of nerve cells of the central nervous system. Without intending to be limited by any theory or mechanism of action, it is demonstrated in the examples provided herein that the administration of M-CSF, aka CSF-1, as well as IL-34, both macrophage colony stimulating factor receptor agonists, in various mouse models of neurodegeneration can improve cognitive function, attenuate neuronal damage and/or stimulate neuronal repair. Of crucial importance, the macrophage colony stimulating factor receptor agonists were demonstrated to exert the neuroprotective effects not only when administered before a neuronal insult had occurred, but also following a neuronal insult.

As described in example 1, doses of M-CSF administered to hAPP mice (a well-established mouse model of Alzheimer's disease) improved cognitive function. The administration of M-CSF attenuated neuronal damage in a mouse model of kainic acid-induced neurodegeneration (example 2) and kainic acid-induced microgliosis (example 3), The significance of neuronal M-CSF receptor signaling for neuronal protection and repair was demonstrated in examples 4, 5, and 6 and an involvement of the cAMP responsive element binding protein (CREB) pathway shown in example 7. In example 8, M-CSF and IL-34 are shown to exert neuroprotective effects in cultured neurons against excitotoxic injury. Examples 9 and 10 describe the neuroprotective effects of IL-34 and M-CSF, respectively, in mice following neuronal injury.

Macrophage colony stimulating factor receptor agonists demonstrated neuroprotective effects in vivo, when administered to mice either prior or after neuronal injury.

As detailed in Example 2, recombinant human macrophage colony stimulating factor receptor agonist M-CSF was administered systemically in a mouse model of kainic acid-induced neurodegeneration to explore whether systemically administered M-CSF had neuroprotective effects. Subcutaneous injection of kainic acid into wildtype FVB mice resulted in significant degeneration of neurons in the pyramidal layer (see FIG. 3 A) and reduced hippocampal calbindin immunereactivity (see FIG. 3 C). In contrast, wildtype FVB mice that systemically had been treated with recombinant, human M-CSF 24 h prior to kainic acid administration showed little hippocampal cell loss (see FIG. 3 A and B) and calbindin reduction (see FIG. 3 C and D). In conclusion, the systemic administration of recombinant, human M-CSF attenuated kainic acid-induced excitotoxic injury and provided significant neuroprotection in vivo in FVB mice.

As detailed in Example 10, recombinant human M-CSF exerted strong neuroprotective effects in mice, even if administered up to 6 h after a neurotoxic insult. Mice receiving recombinant human M-CSF at 2 or 6 hours after kainic acid injection showed similar and significant reduction of astrogliosis (see FIG. 19). Reduced neurodegeneration in these mice was confirmed by pathological analysis (data not shown). These results demonstrate that recombinant human M-CSF exerts strong neuroprotective effects, even if administered up to 6 h after a neurotoxic insult.

Interleukin-34, a cytokine which facilitates the growth and survival of monocytes, has been reported to elicit its activity through binding of c-fms (Lin et al., 2008). In cultured macrophages IL-34 shows an ability, equivalent to M-CSF, to support cell growth and survival. It may, however, interact with distinct regions of c-FMS that might be different from the regions M-CSF interacts with and IL-34 might initiate different biological activities and signal activation (Chihara et al., 2010; Wei et al., 2010).

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

Experimental Procedures

The following methods and materials were used in the examples that are described further below.

Mice. The following transgenic mouse lines were used: hAPP mice (line 41) expressing mutated (London V717I and Swedish K670M/N671L) human APP751 under the control of the murine Thy1 promoter (Rockenstein et al., 2001), GFAP-luc mice (Caliper Life Science) (Zhu et al., 2004), op/op mice (Wiktor-Jedrzejczak et al., 1990; Yoshida et al., 1990) (The Jackson's Laboratory), actin-GFP (ACTB-EGFP) mice expressing enhanced green fluorescence protein (EGFP) under the control of a chicken β-actin promoter (Okabe et al., 1997) (The Jackson's Laboratory), CaMKIIα-cre mice (kindly obtained from Dr. Rudolf Jaenisch, Massachusetts Institute of Technology) (Fan et al., 2001), c-fms-iCre mice (Deng et al., 2010), ROSA-stop$^{flox}$-CFP mice (Srinivas et al., 2001), c-fms$^{f/f}$ (loxP-c-fms-loxP) mice (Li et al., 2006) and c-fms knockout mice (Li et al., 2006). c-fms$^{f/f}$ mice were crossed with CaMKIIα-cre mice to generate c-Fms-null mutant mice (c-fms$^{f/f}$-cre). c-Fms reporter (Csf1r-EGFP, macrophage Fas induced apoptosis, MAFIA) mice (Burnett et al., 2004), expressing EGFP under control of the c-fms promoter, were purchased from the Jackson Laboratory under agreement with Ariad Pharmaceuticals (Cambridge, Mass.). The hAPP, c-fms$^{f/f}$, CaMKIIα-cre and MAFIA mice were on C57bl/6 genetic background, and GFAP-luc mice were on FVB/N background. Wildtype FVB/N or C57bl/6 mice were purchased from The Jackson's Laboratory. Mice were 2-3 month of age at the beginning of experiments, except for hAPP mice which were 5.5-6.5 or 18-20-month-old. Animal handling was performed in accordance with institutional guidelines and approved by a local IACUC. All experiments were done in a randomized and blinded fashion.

Kainic acid administration. For FVB/N mice, kainic acid (Tocris, Ellisville, Mo.) was dissolved in distilled water and injected subcutaneously (20 or 30 mg/kg) to induce neurodegeneration (Luo et al., 2006). Seizure activity was monitored every 15 min for 1 h after kainate administration, using a scoring system from 0 to 8 with 0 showing no behavioral changes and 8 showing death (Janumpalli et al., 1998). All kainic acid-injected mice reached at least stage 3. For C57Bl/6 mice, kainic acid (0.50 µl; 0.1 µg/µl) was injected stereotaxically unilaterally into the right dorsal hippocampus (coordinates from bregma: A=−2.0 mm and L=−1.8 mm, from brain surface: H=−2.0 mm) under Isoflurane anesthesia.

Kainic acid was injected over 2 min using a 5-µl Hamilton syringe. After injection, the needle was maintained in situ for an additional 2 min. to limit reflux along the injection track. The skin was closed using adhesive Surgicalblock and each mouse was injected subcutaneously with Buprenex as directed for pain relief. Animals were examined 1-5 days after kainic acid injection.

Treatment with recombinant macrophage colony stimulating factor receptor agonists. Recombinant human M-CSF was provided by Biogen Idec (Biogen Idec, Cambridge, Mass.). Recombinant mouse IL-34 was purchased from R&D Systems. M-CSF was injected intraperitoneally at 800 µg/kg body weight, a dose previously used clinically in bone marrow transplantation patients (Nemunaitis et al., 1993), or, as indicated. IL-34 was injected intraperitoneally at 100 µg/kg body weight. The same volume of PBS was used as a control treatment. KG501 was purchased from Sigma-Aldrich (St. Louis, Mo.) and dissolved in dimethyl sulfoxide (DMSO). For hAPP mice, recombinant human M-CSF was injected intraperitoneally 3 times a week at 800 µg/kg body weight, a dose previously used clinically in bone marrow transplantation patients (Nemunaitis et al., 1993). The same volume of PBS was used as a control treatment. Kainic acid-injured mice received one injection of recombinant human M-CSF at 800 µg/kg body weight unless indicated otherwise.

Behavioral Tests for hAPP mice. The Morris Water Maze (MWM) was used to assess the effect of M-CSF on spatial learning and memory (Adlard et al., 2005). Briefly, after training the mice with a visible platform, animals were subjected to 6 days of place discrimination training using a hidden platform, with four trials per day, followed by a probe trial 24 hr later to assess retention of the task. Data was analyzed using the Ethovision automated tracking system (Noldus Information Technology). There was no significant difference in the swim speed between the different groups of animals across the study.

Osmotic minipump implantation. Mice were anesthetized with isofluorane. Osmotic minipumps (model 2001, duration: 1 wk; Alzet, Cupertino, Calif.) filled with KG501 (1 µl/h, 250 µg/µl, dissolved in DMSO) or DMSO alone, were implanted subcutaneously into the back of wildtype FVB/N mice, and connected to a brain infusion kit that was placed stereotactically in the right lateral ventricle (coordinates from bregma: A=−0.14 mm, L=−0.76 mm; from brain surface: H=−2.5 mm). Two days after implantation, KA (20 mg/kg) was injected subcutaneously. M-CSF was injected (800 µg/kg body weight, i.p.) 2 h before KA. Continuous substance application through the minipump lasted for 5 more days, and then the mice were anesthetized and perfused.

Tissue processing. Mice were anesthetized with 400 mg/kg chloral hydrate (Sigma-Aldrich) and transcardially perfused with 0.9% saline (Luo et al., 2007; Luo et al., 2006). Brains were removed and divided sagitally. One hemibrain was postfixed in phosphate-buffered 4% paraformaldehyde, pH 7.4, at 4° C. for 48 h and sectioned at 40 µm with a Vibratome 2000 (Leica, Allendale, N.J.) and stored in cryoprotective medium; the other hemibrain was snap frozen and stored at −80° C. for biochemical analysis (Luo et al., 2007; Luo et al., 2006).

Determination of cerebral Aβ Levels by ELISA immunoassay analysis. Snap-frozen hippocampi and cortices were homogenized in RIPA buffer followed by 70% formic acid at 0.1 mg weight tissue per 1 ml. Aβ peptides were quantified by ELISA, as described previously (Pickford et al., 2008) using antibody 266 (5 µg/ml, $A\beta_{13-28}$; Elan Pharmaceuticals) as the capture antibody for total $A\beta_{1-x}$, or antibody 21F12 (5 µg/ml, $A\beta_{37-42}$; Elan Pharmaceuticals) as the capture antibody for $A\beta_{x-42}$ and biotinylated 3D6 (2 µg/ml, $A\beta_{1-5}$; Elan Pharmaceuticals) as the detection antibody. After incubation with the secondary antibody, samples were incubated with avidin-HRP (diluted 1:4,000; Vector Laboratories), and the signal was developed using 1-step Turbo™B ELISA solution (Pierce Biotechnology).

Western blotting. Snap-frozen hippocampi were lysed in 200 µl RIPA lysis buffer (500 mM Tris, pH 7.4, 150 mM NaCl, 0.5% sodium deoxycholate, 1% NP-40, 0.1% SDS and complete protease inhibitors (Roche) (Lin et al., 2005). Cell lysates (20 µl) were mixed with 4× NuPage LDS loading buffer (Invitrogen) and loaded on a 3-12% SDS-polyacrylamide gradient gel and subsequently transferred onto a PVDF membrane. The blot was incubated with rabbit polyclonal antibodies against p-CREB (1:500) or c-fms (1:200), and a horseradish peroxidase-conjugated secondary antibody (Amersham, Pharmacia Biotech, Piscataway, N.J.). Protein signals were detected using an ECL kit (Amersham Pharmacia Biotech).

Cresyl Violet staining. Brain sections were mounted on Superfrost plus slides (Fisher Scientific, Pittsburgh, Pa.), air-dried, rehydrated, stained with 0.02% Cresyl Violet (Sigma) in acetate buffer (pH 3.2), then dehydrated through a series of alcohols, cleared in xylene and coverslipped (Luo et al., 2006). Neuronal damage/loss was assessed based on the appearance of gaps or thinning and disappearance of the Nissl substance in the CA1 and CA3 pyramidal cell layers. The lesion area was quantified with Metamorph Imaging software (Molecular Devices, Downington, Pa.).

Immunohistochemistry, image analysis and confocal microscopy. Immunohistochemistry was performed on free-floating sections following standard procedures (Luo et al., 2007; Luo et al., 2006). Primary antibodies were against: Calbindin (1:10,000, Millipore, Billerica, Mass.), CD68 (1:50, Serotec, Raleigh, N.C.), Iba-1 (1:2,500, Wako Chemicals, Richmond, Va.), Cd11b (1:200, Abcam, Cambridge, Mass.), Neuropeptide Y (1:200; Millipore, Billerica, Mass.), M-CSF (1:2000, R & D Systems, Minneapolis, Minn.), p-CREB (Ser 133) (1:1000, Millipore, Billerica, Mass.), EGFP (1:1,000, Invitrogen, Carlsbad, Calif.) and 3D6 (biotinylated; Elan Pharmaceuticals, South San Francisco, Calif.). Six anti-c-Fms antibodies were obtained (Santa Cruz, Catalog # SC-31638 and SC-33358; Upstate/Millipore, Catalog #06-174 and 06-457; Cell Signaling Technology, Catalog #3155; Biogen, generated by New England Peptide, sequence Ac-DPESPGSTC-amide) and tested with brain sections from c-fms knockout mice (Li et al., 2006). After overnight incubation, primary antibody staining was revealed using biotinylated secondary antibodies and the ABC kit (Vector, Burlingame, Calif.) with Diaminobenzidine (DAB, Sigma-Aldrich) or fluorescence conjugated secondary antibodies. The immunoreactivity was quantified as the percent area covered by Metamorph software (Molecular Devices, Sunnyvale, Calif.), as previously described (Luo et al., 2007; Luo et al., 2006). For each staining, a total of three hippocampal brain sections per mouse were analyzed. Colocalization of two antigens was analyzed under a confocal microscope (LSM 510, Carl Zeiss, Thornwood, N.Y.) using LSM Image Browser software (Carl Zeiss).

Parabiosis. Actin-GFP mice were parabiosed with wild-type littermates or hAPP transgenic mice, as previously described (Conboy et al., 2005). Pairs of mice were anesthetized and prepared for surgery. Mirror-image incisions at the left and right flanks, respectively, were made through the skin. Shorter (~1 cm) incisions were made through the abdominal wall. The abdominal openings were sutured together, and the skin of each mouse was stapled (9 mm Autoclip, Clay Adams) to the skin of its parabiont, thereby closing the incision. Each mouse was injected subcutaneously with Baytril antibiotic and Buprenex, as directed for pain and monitored during recovery. Blood circulation was established after about 2 wks, and the mice were analyzed at 6 wks after surgery. To study the effects of M-CSF, M-CSF or PBS as control was administered separately into both parabionts starting at week 2. hAPP parabionts received M-CSF for 4 weeks. For kainic acid injury, actin-GFP mice were crossed with FVB/N mice to increase susceptibility to kainic acid and F1 mice were used for experiments. M-CSF was injected (i.p.) 24 h before kainic acid.

In Vivo bioluminescence imaging. Bioluminescence was detected with the In Vivo Imaging System (Lin et al., 2005; Luo et al., 2007; Luo et al., 2006) (IVIS Spectrum; Caliper Life Science, Alameda, Calif.). Mice were injected intraperitoneally with 150 mg/kg D-luciferin (Xenogen) 10 min before imaging and anesthetized with isofluorane during imaging. Photons emitted from living mice were acquired as photons/s/cm$^2$/steridian (sr) using LIVINGIMAGE software (version 3.1) and integrated over 5 minutes. For photon quantification, a region of interest was manually selected and kept constant for all experiments; the signal intensity was converted into photons/s/mm$^2$/sr. For longitudinal comparison of bioluminescence, baseline imaging was performed 24 h before kainic acid was administered and bioluminescence was expressed as fold induction over baseline levels for each mouse.

Primary neuron culture. Primary hippocampal neurons were isolated from 16 days old CF1 embryos. Twenty-four-well culture plates were coated with 10 mg/ml Poly-L-Lysine (Sigma-Aldrich). Cells were seeded overnight at a density of 30,000 cells/well in DMEM/F-12 medium supplemented with 10% FBS and penicillin/streptomycin, and subsequently maintained in Neurobasal medium containing 2% B27 supplement (Invitrogen). They were aged for 6-7 days or 21-22 days, then challenged with 100 μM NMDA (N-Methyl-D-aspartic acid, Sigma-Aldrich) for 24 h in the presence and absence of M-CSF or IL-34, and assayed for neurotoxicity or neuritic dystrophy, respectively. At the end of treatment, equal volume of 4% PFA was added, plates incubated at room temperature for 15 min and then washed three times with PBS. Cells were kept in the last wash of PBS at 4° C. till being counted or stained. For the neurotoxicity assay, live and dead cells were counted according to their morphologies determined by phase-contrast microscopy (Knowles et al., 2009; Yang et al., 2008). Results were expressed as % live cells. For quantification of neuritic dystrophy, the fixed cells were immunostained with a MAP-2 monoclonal antibody (1:5,000, Sigma-Aldrich). After overnight incubation, primary antibody staining was revealed by an Alexa fluor 488-conjugated secondary antibody (Invitrogen). MAP2 positive dendrites were observed under an invert fluorescence microscope (Olympus). Dendrites were considered dystrophic when they showed a persistent pattern of increased tortuosity (multiple abrupt turns). To quantify neurite curvature, neurite courses were digitized and approximated by a series of connected line segments using ImageJ (NIH). The angle of each segment was determined using a Sigmaplot macro, and the results were averaged to give the 'mean differential curvature' (Knowles et al., 2009; Yang et al., 2008). This parameter reflects the degree of neurite curvature with an increasing value indicating increased curvature. Neurite counting and quantification were performed in randomly selected fields (5 fields/well) in a completely blinded manner.

B103 Neuroblastoma cells. B103 neuroblastoma cells were cultured in Dulbecco's modified Eagle's medium containing 10% fetal calf serum and 1% v/v penicillin/streptomycin (Invitrogen) in a 5% $CO_2$/95% air atmosphere. Ten thousand ($10^4$) cells/well were seeded onto 24 well plates (Corning Incorporated) and cultured for 24 h before NMDA was added. M-CSF or IL-34 was added 2 hrs before NMDA. Following a 24-hr incubation with NMDA, live and dead cells were assessed using calcein-acetoxymethyl ester (CAM) and SYTOX Orange (both from Invitrogen, Carlsbad, Calif.), respectively. CAM is a membrane-permeable, fluorogenic esterase substrate that is hydrolyzed intracellularly to a green fluorescent product (calcein) in live cells. SYTOX Orange is a high-affinity nucleic acid stain that easily penetrates cells with compromised plasma membranes and yet will not cross the membranes of live cells. After incubation with SYTOX Orange, the nucleic acids of dead cells fluoresce bright orange. The live and dead cells were observed under an invert fluorescence microscope (Olympus), where the live cells showed green color and the nuclei of dead cells exhibited orange fluorescence. Five fields were randomly selected from each well and the cell numbers were analyzed by ImageJ (NIH) in a blinded fashion. Cell survival was expressed as the percentage of live cells over total number of the cells.

In situ hybridization. The cultured primary neurons (6-7 days in culture) were fixed with 4% paraformaldehyde. A 48-mer DNA oligonucleotide probe complementary to bases 904-951 of c-fms (Rothwell and Rohrschneider, 1987) was used for in situ hybridization. The antisense oligonucleotide sequence is as follows: 5'-GTTCATGGTGGCCGTGCGTGTGCCAACATCATTGCTGGCCACACAAGA-3'. The probe was labeled at the 3' end with digoxigenin (DIG). After fixation, the cells were washed with PBS and exposed to proteinase K. Prehybridization was performed for 2 h at 42° C. with hybridization solution (Dako, Carpinteria, Calif.). Hybridization (probe concentration, 1 μg/ml) was carried out in a humidified chamber at 42° C. overnight. The hybridization signal was detected by a DIG Nucleic Acid Detection Kit or HNPP Fluorescent Detection Set (both from Roche Applied Science, Indianapolis, Ind.). The corresponding sense oligonucleotide probe was used as a control.

M-CSF ELISA of human plasma. Human plasma samples were obtained from academic centers (Britschgi et al., 2009). Samples were diluted 1:10 and M-CSF was detected by Quantikine ELISA following the producer's manual (R&D Systems).

Data and statistical analysis. Data are presented as mean±SEM. Behavioral measurements were analyzed using Mann-Whitney rank sum test or 2-tailed Student's t test where appropriate. Bonferroni or Turkey post-hoc test was used to compare pairs of groups following ANOVA. Statistical analysis was performed with Graphpad Prism software (version 5). P<0.05 was considered statistically significant.

EXAMPLES

The following examples are put forth to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1

Figure 1:
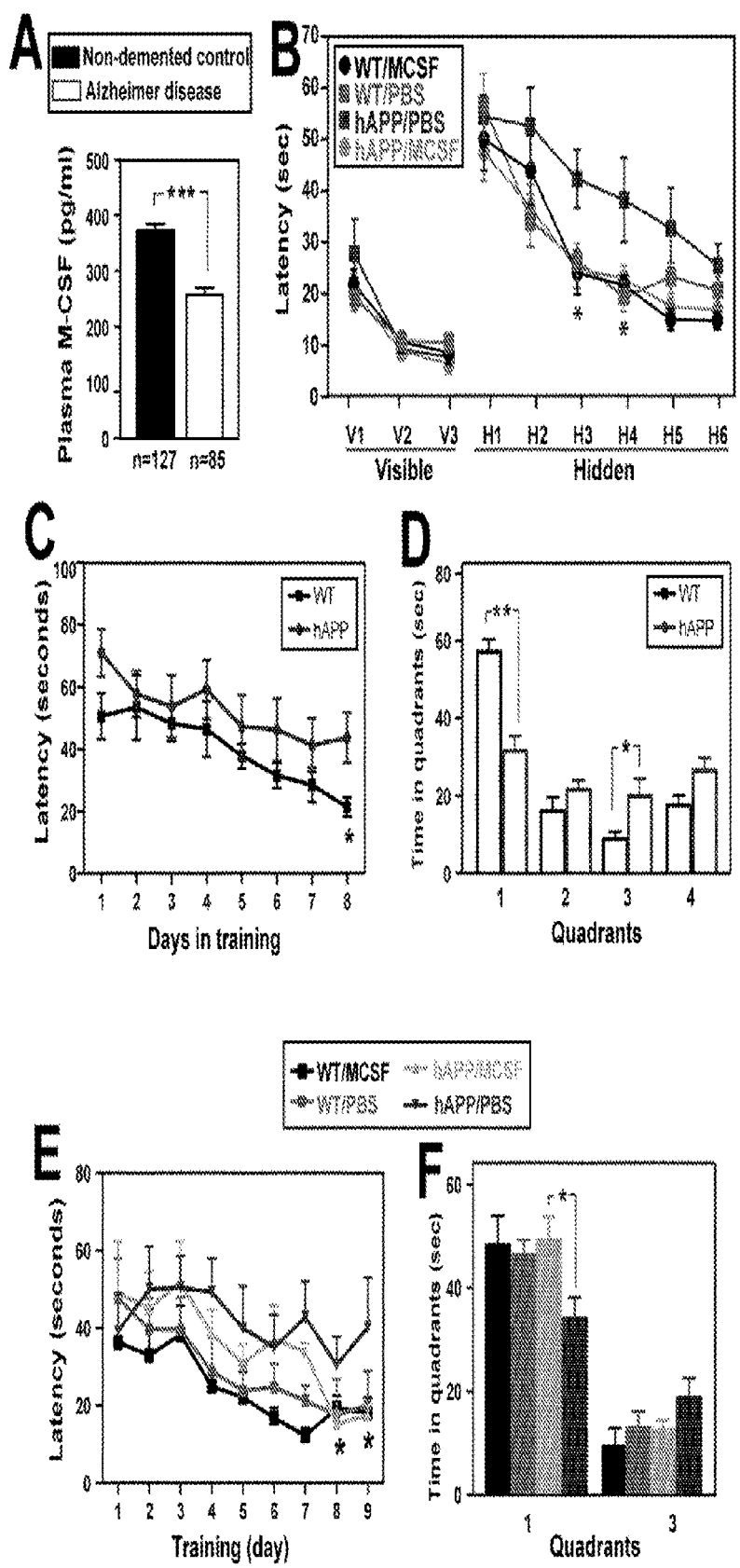
FIG. 1 illustrates the ability of systemically administered macrophage colony stimulating factor (M-CSF) to improve cognitive function in hAPP-transgenic mice, as further described in Example 1. In panel A, M-CSF plasma levels in Alzheimer's disease patients and age-matched non-demented controls are compared. Bars are mean±SEM. ***, $P<0.001$ by Student t test. In panel B, hAPP mice and their wildtype (WT) littermates (n=9-10 mice per genotype, age 5.5-6.5 months) were injected with M-CSF (800 µg/kg) or PBS three times a week. After 10 weeks of treatment spatial cognitive function in mice was assessed using the water maze. In panels C-F, hAPP mice and WT littermates (18-20-month-old) were assessed according to water maze deficits in hidden platform tests (panel C) and a probe trial 24 h later (panel D). The mice were randomly divided into M-CSF or PBS groups (n=6-8 mice per genotype). After a month of treatment, mice were tested again with water maze hidden platform test (panel E) and a probe trial (panel F).

Systemic Administration of Macrophage-Colony Stimulating Factor (M-CSF) Improves Cognitive Function in hAPP-Transgenic Mice, Independent of Aβ Pathology In earlier studies, the inventors of the present invention had observed a decreased concentration of macrophage-colony stimulating factor (M-CSF) in plasma from subjects suffering from Alzheimer's disease ('AD plasma') in comparison to plasma from healthy control subjects ('control plasma'). This observation, in combination with differential concentrations of other signaling proteins in AD plasma versus control plasma can be used to diagnose Alzheimer's disease (Ray et al., 2007). In more recent studies, consistent with these findings, subjects suffering from AD were found to exhibit significantly lower plasma levels of M-CSF than age-matched, healthy control subjects (see FIG. 1A), indicating a peripheral deficiency of M-CSF in subjects suffering from AD.

To investigate in an animal model of Alzheimer's disease the effects of elevated M-CSF concentrations, recombinant M-CSF was administered systemically to hAPP mice. In the hAPP mouse model of Alzheimer's disease mutant human amyloid precursor protein (hAPP) is expressed in neurons under control of the Thy1 promoter (Rockenstein et al., 2001). The hAPP mice, aka Thy1-hAPP transgenic mice, model early Alzheimer's disease-like brain pathology and cognitive impairments. Recombinant human M-CSF or PBS as control was injected intraperitoneally three times a week for 10 weeks into both 6-month-old hAPP mice and their wildtype littermates at a dose of 800 µg/kg body weight; this dosage had been used clinically in human bone marrow transplantation patients (Nemunaitis et al., 1993). After 10 weeks of treatment, all mice were assessed for learning and memory function using the Morris water maze (MWM), a test of spatial learning for rodents that relies on distal cues to navigate from start locations around the perimeter of an open swimming arena to locate a submerged escape platform, and probe trials to assess reference memory (Morris, 1981; Vorhees & Williams, 2006). M-CSF-treated hAPP mice showed significantly better behavioral outcomes than PBS-injected hAPP mice, as indicated by shorter escape latencies in the hidden platform tests (see FIG. 1B).

In further experiments, recombinant human M-CSF or PBS as control (i.p., 800 µg/kg body weight) was injected three times a week into 18-20-month-old hAPP and wildtype mice for only 4 weeks to determine whether M-CSF administration could improve memory function in older animals which already exhibited behavioral deficits (see FIG. 1C/D), and whether a shorter period of treatment would exert similarly beneficial effects. M-CSF treatment significantly reduced memory deficits in hAPP mice in both the Morris Water Maze (see FIG. 1 E) and in the probe trial (see FIG. 1F). Thus, M-CSF treatment had ameliorated learning and memory deficits in hAPP mice in all tested modalities.

To determine whether M-CSF exerted the described beneficial effects by altering Aβ accumulation or aggregation in the brain, both soluble and insoluble levels of Aβ1-x and Aβ1-42 were measured by ELISA immunoassay. No significant changes were observed in the hippocampus or cortex of hAPP mice following M-CSF treatment (Table 1). Similarly, no difference was found in anti-human Aβ1-5 (3D6 antibody) immunoreactivity (see FIG. 2A-C) or the number of plaques in M-CSF compared with PBS injected animals (see FIG. 2D). Therefore, the beneficial effects of M-CSF on cognitive function are likely independent of Aβ accumulation. Moreover, no effects of M-CSF were observed on activation of microglia assessed as a function of CD68 expression by immunoreactivity (Luo et al., 2006); immunoreactivity assessed by percentage of occupied area was 1.152±0.354% in M-CSF-treated hAPP mice vs 0.721±0.169% in PBS-injected group, P=0.289 by t test.

TABLE 1

Effect of M-CSF treatment on cerebral Aβ levels in hAPP mice.
M-CSF treatment did not affect cerebral Aβ levels. hAPP mice and their wildtype (WT) littermates (n = 9-10 mice per genotype, 5.5-6.5 months of age) were injected with M-CSF or PBS (i.p., 800 µg/kg) three times a week for 10 weeks. Mice were sacrificed, and hippocampus and cortex were dissected from one hemibrain. Sequential extractions using RIPA and 70% Formic Acid (FA) buffers were performed on the hemibrains and Aβ was measured by ELISA to detect human Aβ1-x, and Aβ1-42. No significant differences were observed between M-CSF or PBS treated groups.

| Brain Region | Extraction | Groups | $A\beta_{1-x}$ (ng/g) | $A\beta_{1-42}$ (ng/g) |
|---|---|---|---|---|
| Neocortex | RIPA | hAPP/PBS | 13.210 ± 3.070 | 1.324 ± 0.097 |
| | | hAPP/M-CSF | 15.020 ± 2.895 | 1.422 ± 0.214 |
| | FA | hAPP/PBS | 9635.0 ± 1863.0 | 1220.0 ± 245.1 |
| | | hAPP/M-CSF | 11568.0 ± 2493.0 | 1605.0 ± 413.9 |
| Hippocampus | RIPA | hAPP/PBS | 1.018 ± 0.268 | 0.563 ± 0.091 |
| | | hAPP/M-CSF | 1.246 ± 0.198 | 0.731 ± 0.177 |
| | FA | hAPP/PBS | 3539.0 ± 991.7 | 725.5 ± 247.4 |
| | | hAPP/M-CSF | 6879.0 ± 2045.0 | [00109] ± 302.9 |

Values are mean ± SEM; n = 10 for hAPP/PBS, 9 for hAPP/M-CSF.

Example 2

Systemic Administration of M-CSF Reduces Kainic Acid-Induced Neurodegeneration To explore whether systemically administered M-CSF exerts protective effects on neurons, M-CSF was administered systemically in a mouse model of kainic acid-induced neurodegeneration. Subcutaneous administration of kainic acid (20 mg/kg) into wildtype FVB/N mice resulted in severe seizures (highest seizure score 6.4±1.3), with significant degeneration of neurons in the pyramidal layer (FIG. 3A) and reduced hippocampal calbindin immunoreactivity (FIG. 3C) upon postmortem pathological examination, consistent with previous reports (Luo et al., 2006). In contrast, wildtype FVB mice injected intraperitoneally with recombinant, human M-CSF (800 μg/kg body weight) 24 h prior to kainic acid administration showed little hippocampal cell loss (see FIG. 3A/B) and calbindin reduction (see FIG. 3C/D), although they suffered from similar seizure activity (highest seizure score 6.2±1.7). In line with these findings, systemic M-CSF administration significantly reduced the increase in levels of Neuropeptide Y (NPY) in the hippocampus associated with kainic acid lesioning (FIG. 3E/F). Thus, systemic administration of M-CSF attenuated kainic acid-induced excitotoxic neurodegeneration and provided significant neuroprotection in vivo in FVB mice.

Example 3

M-CSF Inhibits Kainic Acid-Induced Microgliosis

Glial cells are non-neuronal cells that surround and insulate neurons from one another, supply oxygen and nutrients to neurons, destroy pathogens and remove dead neurons.

Microglia are the smallest of the glial cells and are generally considered the resident macrophages of the brain and the spinal cord, acting as the first form of active immune defense in the central nervous system. Microglial cells can become activated by a single stimulus such as neuron damage, lipopolysaccharide or kainic acid administration, and in response release neurotoxic factors, including tumor necrosis factor-a, nitric oxide, interleukin-1β, and reactive oxygen species that all drive progressive neuron damage (Lull & Block, 2010); this is known as reactive microgliosis.

Glial cells are sensitive to neuronal dysfunction and damage, and markers associated with activation of microglia are frequently used as indicators of neuronal injury and neurodegeneration (Luo et al., 2006). To investigate whether M-CSF inhibits inflammatory processes, the activation of microglia was analyzed as a function of CD68 immunoreactivity (Luo et al., 2006).

Kainic acid injection into two-months-old FVB/N mice caused massive activation of microglia in the hippocampus (see FIG. 3G/H), which was almost completely prevented by intraperitoneal application of recombinant human M-CSF (see FIG. 3G/H). When microglial activation was quantified with an antibody against the activation marker, CD11b, immunoreactivity, as assessed by percentage of occupied area, was 3.948±0.1997% in the kainic acid/M-CSF-pretreated group versus 4.664±0.04571% in the kainic acid/PBS group (control group), P=0.001 by t test).

In contrast, no difference was found in immunoreactivity for Iba-1, a microglial marker that does not change much in response to activation (immunoreactivity assessed by percentage of occupied area was 0.345±0.009% in the kainic acid/M-CSF-pretreated group versus 0.368±0.007% in the kainic acid/PBS group (control group), P=0.569 by t test), suggesting that the number of microglia was not significantly altered by administration of recombinant human M-CSF.

To investigate whether activated microglia originated from local resident cells or from the periphery and whether the administration of recombinant human M-CSF caused infiltration of peripheral (myeloid) cells into the brain, mice were parabiosed in which two mice share a common blood supply after being joined surgically at their flanks (Conboy et al., 2005). Actin-green fluorescent protein (Actin-GFP) transgenic mice (Okabe et al., 1997) were paired with wildtype mice (see FIG. 4) and wildtype parabionts were analyzed for GFP+ cells in the brain 6 weeks later. In the control parabionts, there were few GFP+ cells in the brain (see FIG. 4B), consistent with previous studies (Ajami et al., 2007), and treatment with recombinant human M-CSF did not significantly increase the number of GFP+ cells. Likewise, no significant difference was detected in the numbers of GFP+ cells in kainic acid-injected mice, with or without prior M-CSF treatment (see FIG. 4B). In addition, similar results were obtained from hAPP parabionts (see FIG. 4B). These data suggest that M-CSF does not exert its neuroprotective effects by recruiting peripheral myeloid or other cells to the brain in response to excitotoxicity or in the hAPP mouse model.

Example 4

The M-CSF Receptor, C-FMS, is Expressed in Neurons and Upregulated Following Neuronal Injury To determine the potential target cell of M-CSF responsible for the beneficial effects in the excitotoxicity model we studied the expression of its receptor, c-Fms, in the brain. We first tested 6 different commercially available c-Fms antibodies, some of which had been used in the literature to stain brain tissues in the past, but found that none of them produced specific staining that was absent in c-Fms knock-out mice (Li et al., 2006). We therefore employed a transgenic reporter mouse, which expresses EGFP under control of the c-fms promoter (Burnett et al., 2004). The expression of EGFP was detected with immunostaining using an anti-GFP antibody, which produced no immunostaining in brains of wildtype mice (FIG. 5). We observed a broad, predominantly microglial expression pattern of the reporter gene throughout the normal, uninjured mouse brain (FIGS. 6A and 5B-5E), consistent with reports in the literature (Raivich et al., 1998; Sherr et al., 1985). Weaker but discernable reporter immunoreactivity was also seen in few, scattered neurons (1.639±0.217%) throughout the brain. In the hippocampus, these neurons were observed in the CA2/3 regions and in the dentate gyrus (FIGS. 6C and 5B-5E). To confirm these findings and validate the reporter mice, we cultured primary hippocampal neurons isolated from these mice and analyzed the expression of c-fms mRNA by in situ hybridization. Seven-day-old primary neurons clearly expressed c-fms mRNA, which was co-localized with EGFP (FIGS. 6E and 7). The expression of c-Fms in neurons was further confirmed in separate lineage tracing studies using a cross between c-fms-iCre and Rosa-flox-stop-CFP mice (FIG. 8). In double transgenic reporter mice, cre recombinase expression in cells with an active c-fms promotor results in deletion of a transcriptional stop sequence and consequent expression of CFP. Again, small numbers of neurons (1.8% in the cortex) throughout the brain showed clear reporter gene expression (FIG. 7).

To determine if c-Fms expression is increased after injury we lesioned mice with kainic acid and found that systemic or intracerebroventricular administration of the toxin, leads to prominent up-regulation of the c-Fms reporter (FIGS. 6B/D, 5B/E, 9). At 6 h after kainic acid administration, reporter expression was increased not only in microglia but clearly also in neurons (36.52±7.125%) (FIGS. 6/D, 5B-E, 9). Reporter expression continued to increase in microglia at 24 h (FIGS. 5B-E) and up until 5 days but decreased again in neurons (data not shown). These results demonstrate that the c-Fms gene is expressed in neurons and upregulated after excitotoxic injury.

Example 5

Depleting M-CSF Receptor (M-CSFR) in Neurons Increases Susceptibility to Excitotoxic Injury To study the potential significance of neuronal M-CSF signaling we deleted the receptor specifically in forebrain neurons. We generated c-Fms-null mutant mice (c-fms$^{f/f}$-cre) by breeding mice with a loxP-c-fms-loxP insertion (Li et al., 2006) (c-fms$^{f/f}$) with CaMKIIα-cre transgenic mice (Fan et al., 2001). We compared c-fms$^{f/f}$-cre mice and their wildtype littermates after stereotaxic injection of PBS into the right and kainic acid (50 ng) into the left dorsal hippocampus (FIG. 10). In spite of similar seizure severity between c-fms$^{f/f}$-cre and wildtype mice (highest seizure score was 4.6±1.5 in wildtype vs 4.9±1.7 in mutant mice), mutant mice died at twice the rate of wildtypes (mortality was 16% in wildtype vs 30% in mutant, P=0.042). Moreover, surviving c-fms$^{f/f}$-cre mice showed significantly more neurodegeneration and neuroinflammation than wildtype littermates (FIG. 11). While cell loss was restricted to the pyramidal cell layer of the CA3 region in wildtype littermates (FIG. 11A), it was more profound and widespread, spanning the whole CA3 and CA1 regions in c-fms$^{f/f}$-cre mice (FIG. 11A/B).

Similarly, calbindin immunoreactivity was depleted more severely in the CA1 subfield in kainic acid injected c-fms$^{f/f}$-cre compared with wildtype littermates (FIG. 11C/D). This increase in susceptibility to excitotoxic neurodegeneration in c-fms$^{f/f}$-cre mice was mirrored by an increase in the microglial response. Microglial activation measured by CD68 expression was markedly increased in c-fms$^{f/f}$-cre compared with wildtype mice (FIG. 11E/F). In wildtype mice, microgliosis was observed only on the ipsilateral side, whereas in c-fms$^{f/f}$-cre mice, it was also observed on the contralateral hippocampus (FIG. 11E). In summary, mice lacking c-Fms in neurons were more susceptible to death and neurodegeneration following excitotoxic injury, supporting a direct protective and survival function of endogenous M-CSF signaling in neurons.

Example 6

Endogenous M-CSF is Upregulated in Neurons Following Neuronal Injury

In the uninjured brain, faint M-CSF immunostaining was observable throughout the brain, which was absent in M-CSF deficient op/op mice (FIG. 12), thus confirming specificity of the antibody. In contrast, kainic acid administration led to a progressive increase of M-CSF immunoreactivity in the hippocampus, first in CA3 at 6 h, and then throughout the hippocampus at 24 h (FIG. 13). M-CSF immunoreactivity was localized mostly to neurons (FIG. 13). While M-CSF expression varied significantly among individual animals immunoreactivity showed a remarkable inverse correlation with neuronal cell loss at day 3 (R=−0.731, P=0.023) (FIG. 13). In agreement with this inverse correlation between M-CSF expression and neurodegeneration we found a striking lack of M-CSF immunoreactivity in mice, which had died within 6 h after kainic acid administration (n=6 mice, FIG. 13A). Together, these results are consistent with the possibility that upregulation of local M-CSF in the brain serves to protect neurons from degeneration and cell death.

Example 7

M-CSF Activates Neuronal CREB Pathway

Further studies were directed to investigate whether M-CSF might act directly on neurons, thereby activating c-Fms coupled intracellular pathways. Of these, cAMP responsive element binding protein (CREB) signaling appears to play a major role in mediating M-CSF's biological effects in macrophages (Casals-Casas et al., 2009). Importantly, kainic acid injury was shown to selectively decrease phosphorylation of CREB (p-CREB) in vulnerable regions but the cause for this decrease was not identified (Ferrer et al., 2002). Since CREB has a key function in neuronal survival (Walton and Dragunow, 2000) we reasoned that M-CSF might activate CREB in neurons as well. Indeed, at 6 h after kainic acid administration, p-CREB immunoreactivity was reduced in CA3 neurons, notably without obvious cell loss at this early time point (FIG. 14A/B). Systemic treatment with M-CSF significantly increased p-CREB immunoreactivity (FIG. 14A/B), and p-CREB protein as measured by Western blot from hippocampal lysates (FIG. 14C/D). These results show that M-CSF can activate CREB in neurons. To confirm the role of CREB in M-CSF mediated neuronal survival, we infused the CREB signaling inhibitor KG501, or PBS as control into the right dorsal hippocampus of wildtype FVB/N mice using osmotic minipumps. KG501 is a small molecule compound that interrupts the interaction between p-CREB and CBP (CREB binding protein) (Best et al., 2004). Kainic acid was subcutaneously administered 2 days after infusion of KG501. Kainate-induced excitotoxic injury was significantly reduced by systemic treatment with M-CSF in PBS-infused controls, but not in KG501-infused animals (FIG. 14E/F). These results show that blocking CREB signaling interferes with the trophic and survival effects of M-CSF and suggests that CREB mediates at least part of the beneficial effects of M-CSF, supporting a direct role of M-CSF in neuronal function.

Example 8

MCSF and IL-34 Protect Neuroblastoma B103 Cells and Primary Neurons Against Excitotoxic Injury and Activate the CREB Pathway To test the possibility that M-CSF acts through neurons, we investigated whether M-CSF possesses the capacity to directly protect neurons from excitotoxicity in cell culture, in the absence of microglia. Indeed, while exposure of B103 neuroblastoma cells to NMDA caused substantial cell death M-CSF significantly reduced cell death (FIGS. 15A/B, 16). Likewise, the newly identified c-Fms ligand IL-34 showed similar protection against NMDA (FIGS. 15B, 16). In line with these findings, incubation with M-CSF or IL-34 significantly increased p-CREB as measured by Western blotting from cell lysates (FIG. 15C). Treatment of cells with GW2580 (Conway et al., 2005), a c-Fms kinase inhibitor, completely blocked M-CSF or IL-34 mediated protection (FIG. 15B). In addition, the CREB inhibitor KG501 also blocked M-CSF or IL-34 mediated protection (FIG. 15B). These results demonstrate that M-CSF, as well as IL-34 can activate CREB signaling via c-Fms receptors and increase survival of neuroblastoma cells injured with excitotoxins.

Similarly, NMDA induced cell death was significantly reduced by M-CSF or IL-34 in primary neurons (FIG. 15D). Moreover, exposure of hippocampal primary neurons to NMDA caused neuritic dystrophy, characterized by the presence of varicosities and excessive tortuosity (FIGS. 15E, 17). These dystrophic changes were prevented almost completely by M-CSF and IL-34 (FIG. 15E, 17). Assessment of dystrophy by visual criteria (FIG. 17E) and by quantification of the neurite mean differential curvature, a measure of tortuosity, showed that M-CSF and IL-34 effectively blocked NMDA-induced dystrophy (FIG. 15F). Taken together, these results show that c-FMS ligands protect cultured neurons against NMDA excitotoxic injury, in part through activation of CREB signaling.

Example 9

Strong Neuroprotective Effects of Systemically Administered IL-34

To determine whether IL-34 provides neuroprotection against excitotoxic injury in vivo we administered recombinant IL-34 (100 µg/kg) systemically in FVB/N mice lesioned by kainate. Mice receiving IL-34 showed significantly reduced neuronal cell loss and calbindin reduction in the pyramidal cell layer of the hippocampus (FIG. 18). These results demonstrate that systemic administration of recombinant IL-34 attenuates excitotoxic injury and provides similar neuroprotection as recombinant M-CSF.

Example 10

Strong Neuroprotective Effects of Recombinant Human M-CSF Administered Post Neuronal Injury Further studies investigated the clinical potential of M-CSF to attenuate neurodegeneration after an injurious insult had occurred. In order to follow injury and neurodegeneration in individual mice over time we used bioluminescent reporter mice expressing luciferase under the control of a GFAP promoter (Luo et al., 2007; Zhu et al., 2004) and administered M-CSF at different time points before or after kainic acid induced injury. Neuronal injury is closely tied to activation of astrocytes and kainic acid-induced bioluminescence in GFAP-luc mice correlates significantly with hippocampal cell death (Zhu et al., 2004). Accordingly, kainic acid injection led to a reproducible, significant increase in bioluminescence in the brain, peaking at 24 h and slowly decreasing until day 5 (FIG. 19A/B). Notably, systemic M-CSF pretreatment (800 µg/kg body weight) at 24 h or 2 h before kainic acid administration significantly inhibited astrogliosis at day 3 and 5, consistent with reduced neuroinflammation and neuronal damage (FIGS. 3 and 19B). Surprisingly, mice receiving M-CSF (800 µg/kg body weight) at 2 or 6 h after kainic acid showed similar and significant reduction of astrogliosis (FIG. 19C). Attenuated neurodegeneration in these mice was confirmed by pathological analysis (FIGS. 19D-G). Thus, these results demonstrate that M-CSF is sufficient to promote neuronal survival and reduce glial activation.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

REFERENCES

Adlard, P. A., Perreau, V. M., Pop, V., and Cotman, C. W. (2005). Voluntary exercise decreases amyloid load in a transgenic model of Alzheimer's disease. *J Neurosci* 25, 4217-4221.

Ajami, B., Bennett, J. L., Krieger, C., Tetzlaff, W., and Rossi, F. M. (2007). Local self-renewal can sustain CNS microglia maintenance and function throughout adult life. *Nature neuroscience* 10, 1538-1543.

Berezovskaya, O., Maysinger, D., and Fedoroff, S. (1995). The hematopoietic cytokine, colony-stimulating factor 1, is also a growth factor in the CNS: congenital absence of CSF-1 in mice results in abnormal microglial response and increased neuron vulnerability to injury. *Int J Dev Neurosci* 13, 285-299.

Berezovskaya, O., Maysinger, D., and Fedoroff, S. (1996). Colony stimulating factor-1 potentiates neuronal survival in cerebral cortex ischemic lesion. *Acta neuropathologica* 92, 479-486.

Best, J. L., Amezcua, C. A., Mayr, B., Flechner, L., Murawsky, C. M., Emerson, B., Zor, T., Gardner, K. H., and Montminy, M. (2004). Identification of small-molecule antagonists that inhibit an activator: coactivator interaction. *Proceedings of the National Academy of Sciences of the United States of America* 101, 17622-17627.

Bhat, R., and Steinman, L. (2009). Innate and adaptive autoimmunity directed to the central nervous system. *Neuron* 64, 123-132.

Boissonneault, V., Filali, M., Lessard, M., Relton, J., Wong, G., and Rivest, S. (2009). Powerful beneficial effects of macrophage colony-stimulating factor on beta-amyloid deposition and cognitive impairment in Alzheimer's disease. *Brain* 132, 1078-1092.

Britschgi, M., Olin, C. E., Johns, H. T., Takeda-Uchimura, Y., LeMieux, M. C., Rufibach, K., Rajadas, J., Zhang, H., Tomooka, B., Robinson, W. H., et al. (2009). Neuroprotective natural antibodies to assemblies of amyloidogenic peptides decrease with normal aging and advancing Alzheimer's disease. *Proceedings of the National Academy of Sciences of the United States of America* 106, 12145-12150.

Burnett, S. H., Kershen, E. J., Zhang, J., Zeng, L., Straley, S. C., Kaplan, A. M., and Cohen, D. A. (2004). Conditional macrophage ablation in transgenic mice expressing a Fas-based suicide gene. *Journal of leukocyte biology* 75, 612-623.

Casals-Casas, C., Alvarez, E., Serra, M., de la Torre, C., Farrera, C., Sanchez-Tillo, E., Caelles, C., Lloberas, J., and Celada, A. (2009). CREB and AP-1 activation regulates MKP-1 induction by LPS or M-CSF and their kinetics correlate with macrophage activation versus proliferation. *European journal of immunology* 39, 1902-1913.

Chihara T et al. (2010). Il-34 and M-CSF share the receptor Fms but are not identical in biological activity and signal activation. *Cell Death Diff* 17:1917-1927.

Chitu, V., and Stanley, E. R. (2006). Colony-stimulating factor-1 in immunity and inflammation. *Current opinion in immunology* 18, 39-48.

Cho, S. J., Zheng, W., Tropsha, A. (1998). Focus-2D: a new approach to the design of targeted combinatorial chemical libraries. *Pac Symp Biocomput* 305-16.

Conboy, I. M., Conboy, M. J., Wagers, A. J., Girma, E. R., Weissman, I. L., and Rando, T. A. (2005). Rejuvenation of aged progenitor cells by exposure to a young systemic environment. *Nature* 433, 760-764.

Conway, J. G., McDonald, B., Parham, J., Keith, B., Rusnak, D. W., Shaw, E., Jansen, M., Lin, P., Payne, A., Crosby, R. M., et al. (2005). Inhibition of colony-stimulating-factor-1 signaling in vivo with the orally bioavailable cFMS kinase inhibitor GW2580. *Proceedings of the National Academy of Sciences of the United States of America* 102, 16078-16083.

Deng, L., Zhou, J. F., Sellers, R. S., Li, J. F., Nguyen, A. V., Wang, Y., Orlofsky, A., Liu, Q., Hume, D. A., Pollard, J. W., et al. (2010). A novel mouse model of inflammatory bowel disease links mammalian target of rapamycin-dependent hyperproliferation of colonic epithelium to inflammation-associated tumorigenesis. *Amer J Pathol* 176: 952-967.

Du Yan, S., Zhu, H., Fu, J., Yan, S. F., Roher, A., Tourtellotte, W. W., Rajavashisth, T., Chen, X., Godman, G. C., Stern, D., and Schmidt, A. M. (1997). Amyloid-beta peptide-receptor for advanced glycation endproduct interaction elicits neuronal expression of macrophage-colony stimulating factor: a proinflammatory pathway in Alzheimer disease. *Proceedings of the National Academy of Sciences of the United States of America* 94, 5296-5301.

Fabene, P. F., Navarro Mora, G., Martinello, M., Rossi, B., Merigo, F., Ottoboni, L., Bach, S., Angiari, S., Benati, D., Chakir, A., et al. (2008). A role for leukocyte-endothelial adhesion mechanisms in epilepsy. *Nature medicine* 14, 1377-1383.

Fan, G., Beard, C., Chen, R. Z., Csankovszki, G., Sun, Y., Siniaia, M., Biniszkiewicz, D., Bates, B., Lee, P. P., Kuhn, R., et al. (2001). DNA hypomethylation perturbs the function and survival of CNS neurons in postnatal animals. *J Neurosci* 21, 788-797.

Ferrer, I., Blanco, R., Carmona, M., Puig, B., Dominguez, I., and Vinals, F. (2002). Active, phosphorylation-dependent MAP kinases, MAPK/ERK, SAPK/JNK and p38, and specific transcription factor substrates are differentially expressed following systemic administration of kainic acid to the adult rat. *Acta neuropathologica* 103, 391-407.

Gowing, G., Lalancette-Hebert, M., Audet, J. N., Dequen, F., and Julien, J. P. (2009). Macrophage colony stimulating factor (M-CSF) exacerbates ALS disease in a mouse model through altered responses of microglia expressing mutant superoxide dismutase. *Experimental neurology* 220, 267-275.

Hamilton, J. A. (1997). CSF-1 signal transduction. *Journal of leukocyte biology* 62, 145-155.

Hamilton, J. A. (2008). Colony-stimulating factors in inflammation and autoimmunity. *Nature reviews* 8, 533-544.

Hidaka, T., Akada, S., Teranishi, A., Morikawa, H., Sato, S., Yoshida, Y., Yajima, A., Yaegashi, N., Okamura, K., and Saito, S. (2003). Mirimostim (macrophage colony-stimulating factor; M-CSF) improves chemotherapy-induced impaired natural killer cell activity, Th1/Th2 balance, and granulocyte function. *Cancer Sci* 94, 814-820.

Imai, Y., and Kohsaka, S. (2002). Intracellular signaling in M-CSF-induced microglia activation: role of Iba1. *Glia* 40, 164-174.

Janumpalli, S., Butler, L. S., MacMillan, L. B., Limbird, L. E., and McNamara, J. O. (1998). A point mutation (D79N) of the alpha2A adrenergic receptor abolishes the antiepileptogenic action of endogenous norepinephrine. *J Neurosci* 18, 2004-2008.

Kandel, E. R. (2001). The molecular biology of memory storage: a dialogue between genes and synapses. *Science* 294, 1030-1038.

Knowles, J. K., Rajadas, J., Nguyen, T. V., Yang, T., LeMieux, M. C., Vander Griend, L., Ishikawa, C., Massa, S. M., Wyss-Coray, T., and Longo, F. M. (2009). The p75 neurotrophin receptor promotes amyloid-beta(1-42)-induced neuritic dystrophy in vitro and in vivo. *J Neurosci* 29, 10627-10637.

Langer, R. (1990). New methods of drug delivery. *Science* 249:1527-1533

Li, J., Chen, K., Zhu, L., and Pollard, J. W. (2006). Conditional deletion of the colony stimulating factor-1 receptor (c-fms proto-oncogene) in mice. *Genesis* 44, 328-335.

Li, M., Pisalyaput, K., Galvan, M., and Tenner, A. J. (2004). Macrophage colony stimulatory factor and interferon-gamma trigger distinct mechanisms for augmentation of beta-amyloid-induced microglia-mediated neurotoxicity. *Journal of neurochemistry* 91, 623-633.

Lin, A. H., Luo, J., Mondshein, L. H., ten Dijke, P., Vivien, D., Contag, C. H., and Wyss-Coray, T. (2005). Global analysis of Smad2/3-dependent TGF-beta signaling in living mice reveals prominent tissue-specific responses to injury. *J Immunol* 175, 547-554.

Lin, H., Lee, E., Hestir, K., Leo, C., Huang, M., Bosch, E., Halenbeck, R., Wu, G., Zhou, A., Behrens, D., et al. (2008). Discovery of a cytokine and its receptor by functional screening of the extracellular proteome. *Science* 320, 807-811.

Lonze, B. E., and Ginty, D. D. (2002). Function and regulation of CREB family transcription factors in the nervous system. *Neuron* 35, 605-623.

Lucin, K. M., and Wyss-Coray, T. (2009). Immune activation in brain aging and neurodegeneration: too much or too little? *Neuron* 64, 110-122.

Lull, M. E. & Block, M. L. (2010). Microglial activation and chronic neurodegeneration. *Neurotherapeutics* 7, 354-365.

Luo, J., Ho, P. P., Buckwalter, M. S., Hsu, T., Lee, L. Y., Zhang, H., Kim, D. K., Kim, S. J., Gambhir, S. S., Steinman, L., and Wyss-Coray, T. (2007). Glia-dependent TGF-beta signaling, acting independently of the TH17 pathway, is critical for initiation of murine autoimmune encephalomyelitis. *The Journal of clinical investigation* 117, 3306-3315.

Luo, J., Lin, A. H., Masliah, E., and Wyss-Coray, T. (2006). Bioluminescence imaging of Smad signaling in living mice shows correlation with excitotoxic neurodegeneration. *Proceedings of the National Academy of Sciences of the United States of America* 103, 18326-18331.

Majumdar, A., Cruz, D., Asamoah, N., Buxbaum, A., Sohar, I., Lobel, P., and Maxfield, F. R. (2007). Activation of microglia acidifies lysosomes and leads to degradation of Alzheimer amyloid fibrils. *Molecular biology of the cell* 18, 1490-1496.

Mattson, M. P. (2004). Pathways towards and away from Alzheimer's disease. *Nature* 430, 631-639.

Maurer, M. H., Schabitz, W. R., and Schneider, A. (2008). Old friends in new constellations—the hematopoetic growth factors G-CSF, GM-CSF, and EPO for the treatment of neurological diseases. *Current medicinal chemistry* 15, 1407-1411.

Michaelson, M. D., Bieri, P. L., Mehler, M. F., Xu, H., Arezzo, J. C., Pollard, J. W., and Kessler, J. A. (1996). CSF-1 deficiency in mice results in abnormal brain development. *Development* 122, 2661-2672.

Morris R G M (1981). Spatial localization does not require the presence of local cues. *Learn. Motiv.* 12, 239-260.

Morrison R S et al. (2002) Neuronal survival and cell death signaling pathways. *Adv. Exp. Med. Biol.* 513, 41-86.

Murase, S., and Hayashi, Y. (1998). Expression pattern and neurotrophic role of the c-fms proto-oncogene M-CSF receptor in rodent Purkinje cells. *J Neurosci* 18, 10481-10492.

Murphy, G. M., Jr., Yang, L., and Cordell, B. (1998). Macrophage colony-stimulating factor augments beta-amyloid-induced interleukin-1, interleukin-6, and nitric oxide production by microglial cells. *The Journal of biological chemistry* 273, 20967-20971.

Murphy, G. M., Jr., Zhao, F., Yang, L., and Cordell, B. (2000). Expression of macrophage colony-stimulating factor receptor is increased in the AbetaPP(V717F) transgenic mouse model of Alzheimer's disease. *The American journal of pathology* 157, 895-904.

Nemunaitis, J., Shannon-Dorcy, K., Appelbaum, F. R., Meyers, J., Owens, A., Day, R., Ando, D., O'Neill, C., Buckner, D., and Singer, J. (1993). Long-term follow-up of patients with invasive fungal disease who received adjunctive therapy with recombinant human macrophage colony-stimulating factor. *Blood* 82, 1422-1427.

Okabe, M., Ikawa, M., Kominami, K., Nakanishi, T., and Nishimune, Y. (1997). 'Green mice' as a source of ubiquitous green cells. *FEBS Lett* 407, 313-319.

Penkowa, M., Poulsen, C., Carrasco, J., and Hidalgo, J. (2002). M-CSF deficiency leads to reduced metallothioneins I and II expression and increased tissue damage in the brain stem after 6-aminonicotinamide treatment. *Experimental neurology* 176, 308-321.

Pickford, F., Masliah, E., Britschgi, M., Lucin, K., Narasimhan, R., Jaeger, P. A., Small, S., Spencer, B., Rockenstein, E., Levine, B., and Wyss-Coray, T. (2008). The autophagy-related protein beclin 1 shows reduced expression in early Alzheimer disease and regulates amyloid beta accumulation in mice. *The Journal of clinical investigation* 118, 2190-2199.

Pixley, F. J., and Stanley, E. R. (2004). CSF-1 regulation of the wandering macrophage: complexity in action. *Trends in cell biology* 14, 628-638.

Querfurth, H. W., and LaFerla, F. M. (2010). Alzheimer's disease. *N Engl J Med* 362, 329-344.

Raivich, G., Haas, S., Werner, A., Klein, M. A., Kloss, C., and Kreutzberg, G. W. (1998). Regulation of MCSF receptors on microglia in the normal and injured mouse central nervous system: a quantitative immunofluorescence study using confocal laser microscopy. *J Comp Neurol* 395, 342-358.

Ray, S., Britschgi, M., Herbert, C., Takeda-Uchimura, Y., Boxer, A., Blennow, K., Friedman, L. F., Galasko, D. R., Jutel, M., Karydas, A., et al. (2007). Classification and prediction of clinical Alzheimer's diagnosis based on plasma signaling proteins. *Nature medicine* 13, 1359-1362.

Rockenstein, E., Mallory, M., Mante, M., Sisk, A., and Masliaha, E. (2001). Early formation of mature amyloid-beta protein deposits in a mutant APP transgenic model depends on levels of Abeta(1-42). *Journal of neuroscience research* 66, 573-582.

Rothwell, V. M., and Rohrschneider, L. R. (1987). Murine c-fms cDNA: cloning, sequence analysis and retroviral expression. *Oncogene Res* 1, 311-324.

Ryan, G. R., Dai, X. M., Dominguez, M. G., Tong, W., Chuan, F., Chisholm, O., Russell, R. G., Pollard, J. W., and Stanley, E. R. (2001). Rescue of the colony-stimulating factor 1 (CSF-1)-nullizygous mouse (Csf1(op)/Csf1(op)) phenotype with a CSF-1 transgene and identification of sites of local CSF-1 synthesis. *Blood* 98, 74-84.

Sawada, M., Itoh, Y., Suzumura, A., and Marunouchi, T. (1993). Expression of cytokine receptors in cultured neuronal and glial cells. *Neurosci Lett* 160, 131-134.

Shen, C. J., Rettenmier, C. W., Sacca, R., Roussel, M. F., Look, A. T., and Stanley, E. R. (1985). The c-fms proto-oncogene product is related to the receptor for the mononuclear phagocyte growth factor, CSF-1. *Cell* 41, 665-676.

Sofroniew M V et al. (2001). Nerve growth factor signaling, neuroprotection and neural repair. *Annual review of neuroscience* 24, 1217-1281.

Srinivas S et al. (2001). Cre reporter strains produced by targeted insertion of EYFP and ECFP into the ROSA26 locus. *BMC Dev Biol* 1, 4.

Sun, Y., Ewing, T. J. A., Skillman, A. G., and Kuntz, I. D. (1998). CombiDOCK: Structure-based combinatorial docking and library design. *J Comput Aided Mol Des* 12:597-604.

Takeuchi, A., Miyaishi, O., Kiuchi, K., and Isobe, K. (2001). Macrophage colony-stimulating factor is expressed in neuron and microglia after focal brain injury. *Journal of neuroscience research* 65, 38-44.

Vorhees C V & Williams M T (2006). Morris water maze: procedures for assessing spatial and related forms of learning and memory. *Nature Protocols* 1, 848-858.

Walton M R & Dragunow I (2000). Is CREB a key to neuronal survival? *Trends in neurosciences* 23, 48-53.

Wang, Y., Berezovska, O., and Fedoroff, S. (1999). Expression of colony stimulating factor-1 receptor (CSF-1R) by CNS neurons in mice. *Journal of neuroscience research* 57, 616-632.

Wei S et al. (2010). Functional overlap but differential expression of CSF-1 and IL-34 in their CSF-1 receptor-mediated regulation of myeloid cells. *J Leukocyt Biol* 88:495-505.

Wiktor-Jedrzejczak, W., Bartocci, A., Ferrante, A. W., Jr., Ahmed-Ansari, A., Sell, K. W., Pollard, J. W., and Stanley, E. R. (1990). Total absence of colony-stimulating factor 1 in the macrophage-deficient osteopetrotic (op/op) mouse. *Proceedings of the National Academy of Sciences of the United States of America* 87, 4828-4832.

Wyss-Coray, T. (2006). Inflammation in Alzheimer disease: driving force, bystander or beneficial response? *Nat Med* 12, 1005-1015.

Yang, T., Knowles, J. K., Lu, Q., Zhang, H., Arancio, O., Moore, L. A., Chang, T., Wang, Q., Andreasson, K., Rajadas, J., et al. (2008). Small molecule, non-peptide p75 ligands inhibit Abeta-induced neurodegeneration and synaptic impairment. *PLoS One* 3, e3604.

Yoshida, H., Hayashi, S., Kunisada, T., Ogawa, M., Nishikawa, S., Okamura, H., Sudo, T., Shultz, L. D., and Nishikawa, S. (1990). The murine mutation osteopetrosis is in the coding region of the macrophage colony stimulating factor gene. *Nature* 345, 442-444.

Zhu, L., Ramboz, S., Hewitt, D., Boring, L., Grass, D. S., and Purchio, A. F. (2004). Non-invasive imaging of GFAP expression after neuronal damage in mice. *Neurosci Lett* 367, 210-212.

What is claimed is:

1. A method of attenuating neuronal damage in a human subject following acute central nervous system injury, the method comprising administering a pharmaceutical composition comprising at least one macrophage colony stimulating factor receptor agonist to said human within a predetermined time period following said acute central nervous system injury, wherein said macrophage colony stimulating factor receptor agonist is Interleukin-34 (IL-34) or a biologically active fragment thereof.

2. The method of claim 1, wherein said acute central nervous system injury is caused by a traumatic brain injury, cerebral ischemia, cerebral glucose deprivation, cerebral oxidative stress, spinal cord injury or excitotoxic injury.

3. The method of claim 1, wherein the agonist comprises IL-34.

4. The method of claim 1, wherein the agonist comprises a biologically active fragment of IL-34.

5. A method of stimulating neuronal repair in a human subject following acute central nervous system injury, the method comprising administering a pharmaceutical composition comprising at least one macrophage colony stimulating factor receptor agonist to said human within a predetermined time period following said acute central nervous system injury, wherein said macrophage colony stimulating factor receptor agonist is Interleukin-34 (IL-34) or a biologically active fragment thereof.

6. The method of claim 5, wherein said acute central nervous system injury is caused by a traumatic brain injury, cerebral ischemia, cerebral glucose deprivation, cerebral oxidative stress, spinal cord injury or excitotoxic injury.

7. The method of claim 5, wherein the agonist comprises IL-34.

8. The method of claim 5, wherein the agonist comprises a biologically active fragment of IL-34.

9. A method of stimulating neuronal repair in a human subject suffering from Alzheimer's disease, the method comprising administering a pharmaceutical composition comprising at least one macrophage colony stimulating factor receptor agonist to said human during the course of said Alzheimer's disease, wherein said macrophage colony stimulating factor receptor agonist is Interleukin-34 (IL-34) or a biologically active fragment thereof.

10. The method of claim 9, wherein the agonist comprises IL-34.

11. The method of claim 9, wherein the agonist comprises a biologically active fragment of IL 34.

12. A method of attenuating neuronal damage in a human subject at risk of Alzheimer's disease, the method comprising administering a pharmaceutical composition comprising at least one macrophage colony stimulating factor receptor agonist to said human subject prior to onset of Alzheimer's disease, wherein said macrophage colony stimulating factor receptor agonist is Interleukin-34 (IL-34) or a biologically active fragment thereof.

13. The method of claim 12, wherein the agonist comprises IL-34.

14. The method of claim 12, wherein the agonist comprises a biologically active fragment of IL-34.

15. A method of attenuating neuronal damage in a human subject suffering from Alzheimer's disease, the method comprising administering a pharmaceutical composition comprising at least one macrophage colony stimulating factor receptor agonist to said human subject during the course of said Alzheimer's disease, wherein said macrophage colony stimulating factor receptor agonist is Interleukin-34 (IL-34) or a biologically active fragment thereof.

* * * * *